United States Patent
Pack et al.

(10) Patent No.: US 9,404,097 B2
(45) Date of Patent: Aug. 2, 2016

(54) PEPTIDE CAPABLE OF SILICA DEPOSITION AND USE THEREOF

(71) Applicant: Korea University Research and Business Foundation, Seoul (KR)

(72) Inventors: Seung Pil Pack, Yeongi-gun (KR); Mi Ran Ki, Yeongi-gun (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 75 days.

(21) Appl. No.: 14/348,322

(22) PCT Filed: Oct. 2, 2012

(86) PCT No.: PCT/KR2012/007976
§ 371 (c)(1),
(2) Date: Mar. 28, 2014

(87) PCT Pub. No.: WO2013/048222
PCT Pub. Date: Apr. 4, 2013

(65) Prior Publication Data
US 2014/0255309 A1 Sep. 11, 2014

(30) Foreign Application Priority Data

Sep. 30, 2011 (KR) .................. 10-2011-0100176
Sep. 30, 2011 (KR) .................. 10-2011-0100177

(51) Int. Cl.
*C12N 9/12* (2006.01)
*C07K 14/00* (2006.01)
*C07K 14/405* (2006.01)
*C07K 17/14* (2006.01)

(52) U.S. Cl.
CPC ............. *C12N 9/1205* (2013.01); *C07K 14/00* (2013.01); *C07K 14/405* (2013.01); *C07K 17/14* (2013.01); *C07K 2319/735* (2013.01)

(58) Field of Classification Search
None
See application file for complete search history.

(56) References Cited

U.S. PATENT DOCUMENTS

2011/0229576 A1   9/2011   Trogler et al.

FOREIGN PATENT DOCUMENTS

| KR | 20110129078 A | 12/2011 |
| WO | WO-03099843 A2 | 12/2003 |
| WO | WO-2005105672 A1 | 11/2005 |
| WO | WO-2007089084 A1 | 8/2007 |

OTHER PUBLICATIONS

Belton et al. "Towards an Understanding of (Bio)Silicification: The Role of Amino Acids and Lysine Oligomers in Silification." *J. Mater. Chem.* 14(2004):2231-2241.
Cha et al. "Biomimetic Synthesis of Ordered Silica Structures Mediated by Block Copolypeptides." *Nature.* 403(2000):289-292.
Kröger et al. "Polycationic Peptides from Diatom Biosilica That Direct Silica Nanosphere Formation." *Science.* 286(1999):1129-1132.
Luckarift et al. "Enzyme Immobilization in a Biomimetic Silica Support." *Nat. Biotechnol.* 22.2(2004):211-213.
Naik et al. "Entrapment of Enzymes and Nanoparticles Using Biomimetically Synthesized Silica." *Chem. Comm.* 7.15(2004):1684-1685.
Poulsen et al. "Protein Synthesis, Post-Translation Modification, and Degradation: Silica Morphogenesis by Alternative Processing of Silaffins in the Diatom *Thalassiosira pseudonana.*" *J. Biol. Chem.* 279(2004):42993-42999.
Sarin et al. "Inhibition of Acquired Immunodeficiency Syndrome Virus by Oligodeoxynucleoside Methylphosphonates." *PNAS.* 85(1988):7448-7451.
Shimizu et al. "Silicatein α: Cathepsin L-like Protein in Sponge Biosilica." *PNAS.* 95(1998):6234-6238.
Stein et al. "Physicochemical Properties of Phosphorothioate Oligodeoxynucleotides." *Nucleic Acids Res.* 16.8(1988):3209-3221.

*Primary Examiner* — Thomas S Heard
(74) *Attorney, Agent, or Firm* — Mintz Levin Cohn Ferris Glovsky and Popeo, P.C.; Fred C. Hernandez; Linyu L. Mitra

(57) ABSTRACT

A peptide for synthesizing silica and use thereof are provided. The peptide for synthesizing silica can polymerize silica from a silica precursor in an aqueous solution having conditions of normal temperature, normal pressure and near-neutral weak base. The peptide for synthesizing silica can form a self-assembled structure during silica synthesis, and thus can be used as various biomaterials such as a silica-based protein immobilizer, a biosensor, and a drug delivery system.

7 Claims, 9 Drawing Sheets

FIG.8

```
  M   L   S   K   D   I   I   K   L   L   N   E   Q   V   N   K   E   M   N   S    20
ATGTTATCAAAAGACATCATTAAGTTGCTAAACGAACAAGTGAATAAGGAAATGAACTCT                        60

S   N   L   Y   M   S   M   S   S   W   C   Y   T   H   S   L   D   G   A   G    40
TCCAACTTGTATATGAGCATGAGTTCATGGTGCTATACCCATAGCTTAGATGGCGCGGGG                        120

L   F   L   F   D   H   A   A   E   E   Y   E   H   A   K   K   L   I   I   F    60
CTTTTCTTGTTTGACCATGCGGCTGAAGAATACGAGCATGCTAAAAAGCTTATTATCTTC                        180

L   N   E   N   N   V   P   V   Q   L   T   S   I   S   A   P   E   H   K   F    80
TTGAATGAAAACAATGTGCCTGTGCAATTGACTAGCATCAGCGCGCCTGAGCATAAGTTT                        240

E   G   L   T   Q   I   F   Q   K   A   Y   E   H   E   Q   H   I   S   E   S    100
GAAGGTTTGACTCAAATTTTCCAAAAAGCCTATGAACATGAGCAACACATCAGCGAGTCT                        300

I   N   N   I   V   D   H   A   I   K   S   K   D   H   A   T   F   N   F   L    120
ATTAACAATATCGTCGATCACGCCATAAAAAGCAAAGATCATGCGACTTTGAATTTCTTG                        360

Q   W   Y   V   A   E   Q   H   E   E   E   V   L   F   K   D   I   L   D   K    140
CAATGGTATGTGGCTGAACAGCATGAAGAAGAAGTGCTTTTCAAGGATATTTTGGATAAA                        420

I   E   L   I   G   N   E   N   H   G   L   Y   L   A   D   Q   Y   V   K   G    160
ATTGAGTTGATTGGTAATGAAAACCATGGCTTGTATTTAGCCGATCAGTATGTCAAAGGG                        480

I   A   K   S   R   K   S   *    167
ATCGCTAAAAGCAGGAAATCTTAA          504
```

FIG.9

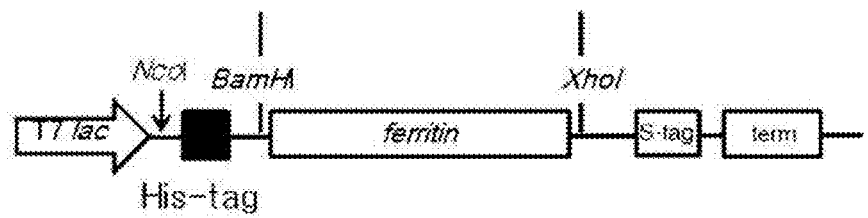

MGSSHHHHHHSQDPMLSKDIIKLLNEQVNKEMNSSNLYMSMSSWCYTHSLDGAGLFLFDHAAEEYEHAKK
LIVFLNENNVPVQLTSISAPEHKFEGLTQIFQKAYEHEQHISESINNIVDHAIKSKDHATFNFLQWYVAEQHEEE
VLFKDILDKIELIGNE NHGLYLADQYVKGIAKSRKS

FIG.10

>sp|Q9SE35|201-219 (R5)
S  S  K  K  S  G  S  Y  S  G  S  K  G  S  K  R  R  I  L
AGCAGCAAAAAAGCGGCAGCTATAGCGGCAGCAAAGGCAGCAAACGCCGCATTCTG

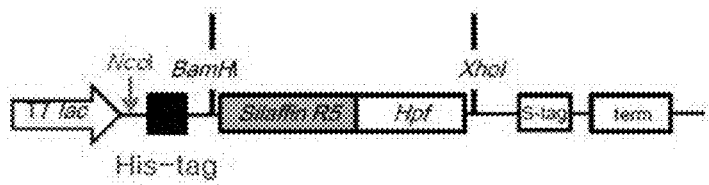

MGSSHHHHHHSQDPSSKKSGSYSGSKGSKRRILLSKDIIKLLNEQVNKEMNSSNLYMSM
SSWCYTHSLDGAGLFLFDHAAEEYEHAKKLIVFLNENNVPVQLTSISAPEHKFEGLTQIF
QKAYEHEQHISESINNIVDHAIKSKDHATFNFLQWYVAEQHEEEVLFKDILDKIELIGNE
NHGLYLADQYVKGIAKSRKS*

FIG.11

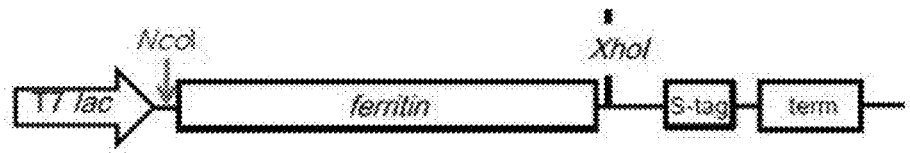

MLSKDIIKLLNEQVNKEMNSSNLYMSMSSWCYTHSLDGAGLFLFDHAA
EEYEHAKKLIVFLNENNVPVQLTSISAPEHKFEGLTQIFQKAYEHEQHISESI
NNIVDHAIKSKDHATFNFLQWYVAEQHEEEVLFKDILDKIELIGNE NHGLY
LADQYVKGIAKSRKS

SEQUENCE LISTING

```
<160> NUMBER OF SEQ ID NOS: 18

<210> SEQ ID NO 1
<211> LENGTH: 26
<212> TYPE: PRT
<213> ORGANISM: Salpingoeca sp.
<220> FEATURE:
<221> NAME/KEY: PEPTIDE
<222> LOCATION: (1)..(26)
<223> OTHER INFORMATION: CAMK/TSSK protein kinase

<400> SEQUENCE: 1

Arg Arg Arg Arg Gly Cys Gly Arg Arg Gly Gly Arg Gly Gly
1               5                   10                  15

Arg Gly Arg Gly Gly Cys Gly Arg Arg Arg
            20                  25

<210> SEQ ID NO 2
<211> LENGTH: 20
<212> TYPE: PRT
<213> ORGANISM: Salpingoeca sp.
<220> FEATURE:
<221> NAME/KEY: PEPTIDE
<222> LOCATION: (1)..(20)
<223> OTHER INFORMATION: CAMK/TSSK protein kinase

<400> SEQUENCE: 2

Cys Gly Arg Arg Arg Gly Gly Arg Gly Gly Arg Gly Arg Gly Gly Cys
1               5                   10                  15

Gly Arg Arg Arg
            20

<210> SEQ ID NO 3
<211> LENGTH: 19
<212> TYPE: PRT
<213> ORGANISM: Ectocarpus siliculosus
<220> FEATURE:
<221> NAME/KEY: PEPTIDE
<222> LOCATION: (1)..(19)
<223> OTHER INFORMATION: Hypothetical protein Esi_0050_0074

<400> SEQUENCE: 3

Ser Ser Arg Ser Ser Ser His Arg Arg His Asp His His Asp His Arg
1               5                   10                  15

Arg Gly Ser

<210> SEQ ID NO 4
```

```
<211> LENGTH: 13
<212> TYPE: PRT
<213> ORGANISM: Ectocarpus siliculosus
<220> FEATURE:
<221> NAME/KEY: PEPTIDE
<222> LOCATION: (1)..(13)
<223> OTHER INFORMATION: Hypothetical protein Esi_0050_0074

<400> SEQUENCE: 4

Ser Ser Lys Lys Ser Gly Glu Arg His His Arg Ser Ala
1               5                   10

<210> SEQ ID NO 5
<211> LENGTH: 15
<212> TYPE: PRT
<213> ORGANISM: Volvox carteri f. nagariensis
<220> FEATURE:
<221> NAME/KEY: PEPTIDE
<222> LOCATION: (1)..(15)
<223> OTHER INFORMATION: Hypothetical protein VOLCADRAFT_33984

<400> SEQUENCE: 5

Ser Gly Arg Arg Arg Gly Ser Arg Arg Gly Ser Arg Arg
1               5                   10              15

<210> SEQ ID NO 6
<211> LENGTH: 14
<212> TYPE: PRT
<213> ORGANISM: Volvox carteri f. nagariensis
<220> FEATURE:
<221> NAME/KEY: PEPTIDE
<222> LOCATION: (1)..(14)
<223> OTHER INFORMATION: Hypothetical protein VOLCADRAFT_95499

<400> SEQUENCE: 6

Ser Arg Leu Arg Gly Arg Arg Arg Arg Leu Ser Pro Gly Arg
1               5                   10

<210> SEQ ID NO 7
<211> LENGTH: 14
<212> TYPE: PRT
<213> ORGANISM: Volvox carteri f. nagariensis
<220> FEATURE:
<221> NAME/KEY: PEPTIDE
<222> LOCATION: (1)..(14)
<223> OTHER INFORMATION: Hypothetical protein VOLCADRAFT_95499

<400> SEQUENCE: 7

Ser Ser His Arg His His His Asp His His Asp His His His
1               5                   10

<210> SEQ ID NO 8
<211> LENGTH: 19
<212> TYPE: PRT
<213> ORGANISM: Cylindrotheca fusiformis
<220> FEATURE:
<221> NAME/KEY: PEPTIDE
<222> LOCATION: (1)..(19)
<223> OTHER INFORMATION: Silaffin R5

<400> SEQUENCE: 8

Ser Ser Lys Lys Ser Gly Ser Tyr Ser Gly Ser Lys Gly Ser Lys Arg
1               5                   10                  15

Arg Ile Leu

<210> SEQ ID NO 9
<211> LENGTH: 14
<212> TYPE: PRT
```

<213> ORGANISM: Artificial Sequence
<220> FEATURE:
<223> OTHER INFORMATION: His-tag peptide

<400> SEQUENCE: 9

Met Gly Ser Ser His His His His His His Ser Gln Asp Pro
1               5                   10

<210> SEQ ID NO 10
<211> LENGTH: 33
<212> TYPE: PRT
<213> ORGANISM: Artificial Sequence
<220> FEATURE:
<223> OTHER INFORMATION: His-tag peptide linked to silaffin R5 from
      Cylindrotheca fusiformis

<400> SEQUENCE: 10

Met Gly Ser Ser His His His His His His Ser Gln Asp Pro Ser Ser
1               5                   10                  15

Lys Lys Ser Gly Ser Tyr Ser Gly Ser Lys Gly Ser Lys Arg Arg Ile
            20                  25                  30

Leu

<210> SEQ ID NO 11
<211> LENGTH: 504
<212> TYPE: DNA
<213> ORGANISM: Helicobacter pylori 26695
<220> FEATURE:
<221> NAME/KEY: gene
<222> LOCATION: (1)..(504)
<223> OTHER INFORMATION: pfr gene

<400> SEQUENCE: 11

```
atgttatcaa aagacatcat taagttgcta aacgaacaag tgaataagga aatgaactct      60
tccaacttgt atatgagcat gagttcttgg tgctataccc atagcttaga tggctcgggg     120
cttttcttgt ttgaccatgc ggctgaagaa tacgagcatg ctaaaaagct tatcgttttc     180
ttgaatgaaa acaatgtgcc tgtgcaattg accagcatca gcgcgcctga gcataagttt     240
gaaagcttga ctcaaatttt ccaaaaagcc tatgaacatg agcaacacat cagcgagtct     300
attaataata tcgtcgatca cgccataaaa agcaaagatc atgcgacttt caatttcttg     360
caatggtatg tggctgaaca gcatgaagaa gaagtgcttt tcaaggatat tttggataaa     420
attgagttga ttggtaatca aaaccatggc ttgtatttgg ctgatcagta tgtcaaaggg     480
atcgctaaaa gcaggaaatc ttaa                                            504
```

<210> SEQ ID NO 12
<211> LENGTH: 167
<212> TYPE: PRT
<213> ORGANISM: Helicobacter pylori 26695
<220> FEATURE:
<221> NAME/KEY: PEPTIDE
<222> LOCATION: (1)..(167)
<223> OTHER INFORMATION: pfr

<400> SEQUENCE: 12

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
            20                  25                  30

Thr His Ser Leu Asp Gly Ser Gly Leu Phe Leu Phe Asp His Ala Ala
        35                  40                  45

```
Glu Glu Tyr Glu His Ala Lys Lys Leu Ile Val Phe Leu Asn Glu Asn
 50                  55                  60

Asn Val Pro Val Gln Leu Thr Ser Ile Ser Ala Pro Glu His Lys Phe
 65                  70                  75                  80

Glu Ser Leu Thr Gln Ile Phe Gln Lys Ala Tyr Glu His Glu Gln His
                 85                  90                  95

Ile Ser Glu Ser Ile Asn Asn Ile Val Asp His Ala Ile Lys Ser Lys
                100                 105                 110

Asp His Ala Thr Phe Asn Phe Leu Gln Trp Tyr Val Ala Glu Gln His
            115                 120                 125

Glu Glu Glu Val Leu Phe Lys Asp Ile Leu Asp Lys Ile Glu Leu Ile
        130                 135                 140

Gly Asn Gln Asn His Gly Leu Tyr Leu Ala Asp Gln Tyr Val Lys Gly
145                 150                 155                 160

Ile Ala Lys Ser Arg Lys Ser
                165
```

<210> SEQ ID NO 13
<211> LENGTH: 14
<212> TYPE: PRT
<213> ORGANISM: Artificial Sequence
<220> FEATURE:
<223> OTHER INFORMATION: GS peptide

<400> SEQUENCE: 13

```
Gly Ser Ser Ser Ser Gly Ser Ser Ser Ser Asn Asn Lys
  1               5                  10
```

<210> SEQ ID NO 14
<211> LENGTH: 39
<212> TYPE: DNA
<213> ORGANISM: Artificial Sequence
<220> FEATURE:
<223> OTHER INFORMATION: PF primer

<400> SEQUENCE: 14
cgggatccga tgttatcaaa agacatcatt aagttgcta                    39

<210> SEQ ID NO 15
<211> LENGTH: 37
<212> TYPE: DNA
<213> ORGANISM: Artificial Sequence
<220> FEATURE:
<223> OTHER INFORMATION: PR primer

<400> SEQUENCE: 15
ccgctcgagt cattaagatt tcctgctttt agcgatc                      37

<210> SEQ ID NO 16
<211> LENGTH: 55
<212> TYPE: DNA
<213> ORGANISM: Artificial Sequence
<220> FEATURE:
<223> OTHER INFORMATION: SPF primer

<400> SEQUENCE: 16
cagcaaaggc agcaaacgcc gcattctgtt atcaaaagac atcattaagt tgcta   55

<210> SEQ ID NO 17
<211> LENGTH: 66
<212> TYPE: DNA
<213> ORGANISM: Artificial Sequence
<220> FEATURE:

```
<223> OTHER INFORMATION: SF primer

<400> SEQUENCE: 17
cgggatccga gcagcaaaaa aagcggcagc tatagcggca gcaaaggcag caaacgccgc    60
attctg                                                              66

<210> SEQ ID NO 18
<211> LENGTH: 43
<212> TYPE: DNA
<213> ORGANISM: Artificial Sequence
<220> FEATURE:
<223> OTHER INFORMATION: BsaI_PF primer

<400> SEQUENCE: 18
gcccctctcg gtctcccatg ttatcaaaag acatcattaa gtt                     43
```

PEPTIDE CAPABLE OF SILICA DEPOSITION AND USE THEREOF

CROSS-REFERENCE TO RELATED APPLICATION

This application is a national stage application, filed under 35 U.S.C. §371, of International Application No. PCT/KR2012/007976, filed Oct. 2, 2012, which claims priority to and the benefit of Korean Patent Application No. 2011-0100176, filed Sep. 30, 2011 and Korean Patent Application No. 2011-0100177, filed Sep. 30, 2011, the contents of each of which are incorporated by reference in their entireties.

INCORPORATION-BY-REFERENCE OF SEQUENCE LISTING

The contents of the text file named "46278-512N01US_ST25.txt", which was created on Mar. 28, 2014 and is 8 KB in size, are hereby incorporated by reference in their entireties.

BACKGROUND

1. Field of the Invention

The present invention relates to a peptide capable of synthesizing silica from a silica precursor in an aqueous solution whose conditions include normal temperature, a normal pressure and a near-neutral weak base, and use thereof.

2. Discussion of Related Art

Development of new useful resources has been raised as an important national issue for the future due to the exhaustion of ground resources materials caused by a sudden increase in consumption of limited available resources after the industrialization. Therefore, advanced countries such as US, EU and Japan has focused their national capacities to develop and ensure new source materials. In addition, as global warming and climate change caused by the environmental pollution serve as factors which threaten the survival of the human race, a new paradigm has appeared to seek for the economic growth and protection of environment at the same time.

A method of producing a new material through environmentally friendly biological production using marine resources is expected to be a technique for playing important roles in ensuring original technology and achieving national low-carbon green growth with growth of environmentally friendly industries. Since silica is able to covalently bind to certain chemical species, it plays an important role in synthesis of a new hybrid material (i.e., an organic-inorganic complex), and also has an excellent characteristic of making up for the weak points of respective materials as biocompatible materials. In recent years, an industrial production process of silica has problems in that it requires the conditions of high temperature, and strong acid or base, and environmentally harmful by-products may be produced.

However, as enzymes and peptides for biosynthesizing silica from extracts of marine living organisms such as a sponge and a diatom or based on their genetic information have been found, development of a marine-derived bio-silica composite material has been issued all over the world due to the applicability of an environmentally friendly bio-silica produced by the enzymes and peptides, and various uses thereof (Cha et al., 2000, Nature 403:pp. 289-292; Kroger et al, 1999, Science 286: pp. 1129-1132; Poulsen & Kroger, 2004, J Biol Chem 279: pp. 42993-42999; Shimizu et al, 1998, Proc Natl Acad Sci USA 95: pp. 6234-6238). Since the bio-silica material can be prepared into a proper formulation for various applications, and is expected to exhibit excellent energy efficiency, mechanical/chemical properties, biologically synthetic activities and mass productivity, it is very important to possess the original technology for ensuring a biological catalyst for bio-silica material production.

Silaffin produced by the diatom has 260 amino acid residues, which are degraded into peptides having 7 repeated sequences during a maturation stage. In this case, each of the peptides serves as a template and a catalyst for silica synthesis. Silicatein that is an enzyme for synthesizing silica produced by the sponge has a highly conserved amino acid sequence among the sponge species, but peptides for synthesizing silica produced by the diatom have poorly conserved amino acid sequences but show structural similarities after post-translational modification.

SUMMARY OF THE INVENTION

The present invention is directed to providing a peptide capable of synthesizing silica, and use for preparing multifunctional silica using the same.

Also, the present invention is directed to providing use of a silica-based complex prepared by the peptide in various industrial fields such as electronics, chemistry, pharmaceutics, etc.

To solve the above problems, one aspect of the present invention provides a composition for synthesizing silica, which includes at least one peptide selected from the group consisting of amino acid sequences set forth in SEQ ID NOs: 1 to 7.

The composition for synthesizing silica may further include a silica precursor, an enzyme or a binding peptide, a self-assembling protein, a microstructure such as a nanotube or a nanomesh, a phospholipid, or hydroxyapatite.

Another aspect of the present invention provides a fusion protein including at least one peptide selected from the group consisting of amino acid sequences set forth in SEQ ID NOs: 1 to 10, and a self-assembling protein.

Still another aspect of the present invention provides a composition for synthesizing silica, which includes the fusion protein.

Still another aspect of the present invention provides a method of synthesizing silica, which includes reacting a silica precursor with at least one peptide selected from the group consisting of amino acid sequences set forth in SEQ ID NOs: 1 to 7, or the above mentioned fusion protein.

Still another aspect of the present invention provides a silica complex in which a surface of a self-assembled structure of a peptide selected from the group consisting of amino acid sequences set forth in SEQ ID NOs: 1 to 7 is coated with silica.

The silica complex may have a fluorescent material, a tissue-specific binding component, a pharmaceutically active component, an enzyme or a binding peptide, a microstructure such as a nanotube or a nanomesh, a phospholipid, or hydroxyapatite further bound thereto.

Still another aspect of the present invention provides a silica complex in which surfaces of self-assembled structures of at least one peptide selected from the group consisting of amino acid sequences set forth in SEQ ID NOs: 1 to 10, and a self-assembling protein are coated with silica.

Still another aspect of the present invention provides a drug delivery system including the silica complex and a pharmaceutically acceptable carrier.

Still another aspect of the present invention provides a contrast agent composition including the silica complex and a pharmaceutically acceptable carrier.

Still another aspect of the present invention provides a target-directed contrast agent composition including the silica complex and a pharmaceutically acceptable carrier.

Still another aspect of the present invention provides a contrast agent composition for simultaneous diagnosis or treatment, which includes the silica complex, and a pharmaceutically acceptable carrier.

Still another aspect of the present invention provides a fiber into which the silica complex is electrospun.

Still another aspect of the present invention provides a filter including the fiber into which the silica complex is electrospun.

Still another aspect of the present invention provides a bone substitute including the silica complex.

Still another aspect of the present invention provides a photonic device including the silica complex.

Yet another aspect of the present invention provides a biosensor for detecting a biomolecule, which includes the silica complex.

BRIEF DESCRIPTION OF THE DRAWINGS

FIG. 8 shows pfr gene sequences and coding sequences of Helicobacter pylori (H. pylori) ferritin according to the present invention.

FIG. 9 shows a ferritin-producing vector construct and an amino acid sequence of a produced protein.

FIG. 10 shows the construction of a R5-ferritin synthesis vector according to the present invention, and an amino acid sequence of a produced protein.

FIG. 11 shows a His tag-free ferritin (Pfr) expression vector and a sequence of a produced protein thereof.

DETAILED DESCRIPTION OF EXEMPLARY EMBODIMENTS

Figure 1:
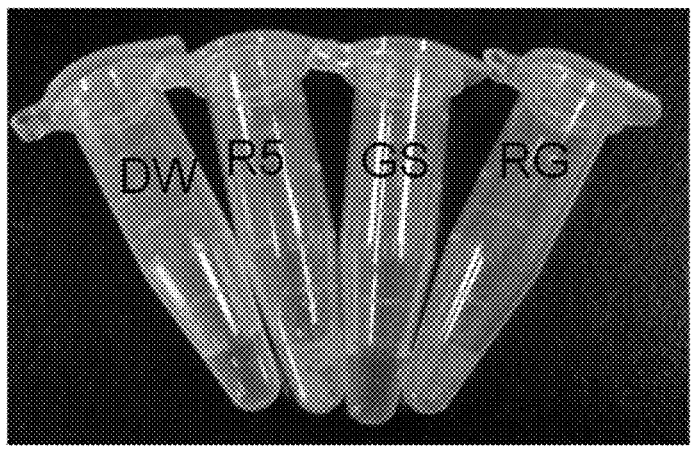
FIG. 1 shows the results of silica synthesis by marine species-derived peptides capable of synthesizing silica, that is, R5, GS and RG peptides, according to the present invention. Here, white precipitates observed in R5 and RG tubes are silica synthetic products.

Unless particularly defined otherwise, all terms including technical and scientific terms used herein have the same meaning as commonly understood by one of ordinary skill in the art to which this invention belongs. In general, the nomenclatures used in this specification and the experimental methods described below are widely known and generally used in the related art.

The definition of the main terms used in the detailed description of the present invention is as described below.

The term "peptide capable of synthesizing silica" or "peptide having silica synthesis activities" generally refers to a peptide capable of synthesizing silica through a reaction with a silica precursor.

The term "self-assembling protein" refers to a protein to which at least one monomer is bound to form a spherical macromolecule having a core-shell structure having a hollow inner space formed therein.

The term "recombinant vector" refers to a vector capable of expressing a target protein in a proper host cell, that is, a gene construct including an essential regulatory element operatively linked to express a gene insert.

Hereinafter, the configurations of the present invention will be described in further detail.

The present inventors assumed that there are various amino acid sequences which can synthesize silica from a variety of marine species and searched for novel peptides capable of synthesizing silica from the NCBI's protein database in the U.S. using peptides having amino acid sequences in which amino acids containing a hydroxyl group (—OH) and an amine group (—NH$_2$), both of which play an important role in post-translation modification, such as serine, lysine, arginine and histidine, are present at high contents, as queries. Therefore, the present invention has been completed based on these facts (blast.ncbi.nlm.nih.gov).

Accordingly, one aspect of the present invention relates to a composition for synthesizing silica including at least one peptide selected from the group consisting of amino acid sequences set forth in SEQ ID NOs: 1 to 7.

The peptide capable of synthesizing silica according to the present invention may be referred to as a peptide derived from a marine living organism, which has an activity to synthesize silica and is set forth in SEQ ID NOs: 1 to 7. The peptide may have one of the amino acid sequences set forth in SEQ ID NOs: 1 to 7, and may also have an amino acid sequence shorter than the amino acid sequences set forth in SEQ ID NOs: 1 to 7 without affecting the innate properties of the peptide. More particularly, the peptide may have at least 5 consecutive amino acid sequences. Further, the peptide may be composed of 5 to 26 consecutive amino acid sequences.

Most particularly, a peptide (hereinafter also referred to as "RG") composed of an amino acid sequence set forth in SEQ ID NO: 1 may have an amino acid sequence corresponding to a $294^{th}$ to $319^{th}$ amino acid sequence of a CAMK/TSSK protein kinase of *Salpingoeca* sp. ATCC 50818 belonging to a member of flagellates, a peptide (hereinafter also referred to as "Sal_p1") composed of an amino acid sequence set forth in SEQ ID NO: 2 may have amino acid sequence corresponding to a $300^{th}$ to $319^{th}$ amino acid sequence whose length is significantly shorter than that of the peptide set forth in SEQ ID NO: 1, a peptide (hereinafter also referred to as Ect_p1) composed of an amino acid sequence set forth in SEQ ID NO: 3 may have an amino acid sequence corresponding to a $2833^{th}$ to $2851^{st}$ amino acid sequence of a protein (Genebank Accession No. CBJ26926) which is derived from a brown algae, *Ectocarpus siliculosus*, and whose functions are not known, a peptide (hereinafter also referred to as Ect_p2) composed of an amino acid sequence set forth in SEQ ID NO: 4 may have an amino acid sequence corresponding to a $1674^{th}$ to $1686^{th}$ amino acid sequence of a protein such as the peptide set forth in SEQ ID NO: 3, a peptide (hereinafter also referred to as Vol_p1) composed of an amino acid sequence set forth in SEQ ID NO: 5 may have an amino acid sequence corresponding to a $10^{th}$ to $24^{th}$ amino acid sequence of a protein (Genebank Accession No. XP_002959480) which is derived from *Volvox* sp. and whose functions are not known, and peptides (hereinafter also referred to as Vol_p2 and Vol_p3, respectively) composed of amino acid sequences set forth in SEQ ID NOs: 6 and 7 may have $461^{st}$ to $474^{th}$ and $630^{th}$ to $643^{rd}$ amino acid sequences which are derived from *Volvox* sp. and whose functions are not known.

The peptide may be prepared using methods of synthesizing a peptide known in the related art. For example, the peptide may be prepared in vitro through genetic recombination, or may be prepared through a method of synthesizing a peptide using a protein expression system or a peptide synthesizer.

The peptide exhibiting the silica synthesis activities may react with a silica precursor in an aqueous solution of weak base under the conditions of normal temperature and normal pressure to synthesize silica.

The aqueous solution is preferably a buffer solution of pH 6 to 8. In this case, the kind and concentration of the buffer solution are not particularly limited, but may vary properly according to applications of the composition for synthesizing silica.

The silica precursor may include tetraethyl orthosilicate, tetramethyl orthosilicate, methyl triethoxy silane, phenyl triethoxy silane, dimethyl dimethoxy silane, ethyl triethoxy silane, titania tetraisopropoxide, and tetraethyl germanium, which may be used alone or in combination.

Also, the peptide exhibiting the silica synthesis activities according to the present invention may be used to immobilize an enzyme or a binding peptide onto the silica.

Therefore, the composition for synthesizing silica according to the present invention may further include an enzyme or a binding peptide.

For this purpose, the enzyme or the binding peptide may be included in the form of a fusion protein obtained by binding a gene coding for the peptide having the silica synthesis activities to a gene coding for the enzyme or the binding peptide, or may be included in a state in which the enzyme or the binding peptide is added and immobilized in a silica complex upon silica synthesis.

The kind of the enzyme may be properly chosen and used according to applications, but the present invention is not particularly limited thereto. For example, horseradish peroxidase may be used.

An antibody, a peptide specifically binding to DNA or RNA, or a receptor may be used as the binding peptide, but the present invention is not particularly limited thereto.

The silica in which the enzyme or the binding peptide is immobilized may be prepared by reacting a silica precursor with the fusion protein so that the fusion protein can be coated with the silica, or may be prepared by mixing and reacting the peptide having the silica synthesis activities, the silica precursor and the enzyme or binding peptide at predetermined mixing ratios and centrifuging the resulting reaction mixture.

Also, the composition for synthesizing silica according to the present invention may further include a self-assembling protein, or a microstructure such as a nanotube or a nanomesh.

The self-assembling protein may be a ferritin, or a viral capsid protein.

The ferritin is a ferritin (HP0653) having an amino acid sequence set forth in SEQ ID NO: 12, which is expressed from a pfr gene of *H. pylori*. In this case, the ferritin serves to store and transfer metal ions, and has an advantage in that the ferritin can be overexpressed in the form of a soluble protein in *Escherichia coli* since the ferritin is derived from a procaryote. Also, the ferritin is characterized in that a peptide or silicatein having silica synthesis activities may be directly bound to the N-terminus of the ferritin without a linker since the N-terminus of the ferritin is exposed to the outside upon self-assembly.

The peptide having the silica synthesis activities may bind to either the N-terminus or the C-terminus, or both of the N-terminus and the C-terminus of a self-assembling protein, or may bind to any one of the N-terminus and the C-terminus of the self-assembling protein via a ligand regardless of binding positions without affecting the innate properties of the peptide. Therefore, the fusion protein of the self-assembling protein and the peptide having the silica synthesis activities refers to all kinds of fusion proteins formed by binding the peptide having the silica synthesis activities to the self-assembling protein regardless of binding positions without affecting the innate properties of the peptide.

The microstructure may include a nanotube or a nanomesh, but the present invention is not particularly limited thereto.

Also, when the silica is synthesized through reaction of the silica precursor with the peptide having the silica synthesis activities, the silica may be used together with a phospholipid so that the silica can be coated as a single film without forming a precipitate.

The single silica film may be obtained by allowing the peptide having the silica synthesis activities, the silica precursor and the phospholipid to react under typical conditions used to synthesize silica.

In addition, a porous silica structure may be prepared by mixing the phospholipid with the peptide having the silica synthesis activities and the silica precursor at proper mixing ratios to form an organic/inorganic complex, and treating the organic/inorganic complex with heat or an organic solvent to remove an organic substance.

Also, the composition for synthesizing silica according to the present invention may be used to synthesize silica using an inorganic substance such as hydroxyapatite in addition to the organic substance, thereby forming a silica complex.

The silica complex may be obtained by allowing the peptide having the silica synthesis activities, the silica precursor and the hydroxyapatite to react under the conventional synthetic conditions of silica.

The silica complex may be applied to a bone substitute and a tooth substitute, and may also be used as a cell culture coating agent in a medium for bone cell differentiation, and used for 3D scaffolds.

The present invention is directed to providing a fusion protein including at least one peptide selected from the group consisting of amino acid sequences set forth in SEQ ID NOs: 1 to 10, and a self-assembling protein.

Also, the present invention is characterized in that it provides a composition for synthesizing silica including the fusion protein.

The peptide having the silica synthesis activities may bind to a self-assembling protein, which can form a self-assembling structure, to form a nanostructure. Such a nanostructure may be formed in the form of a fusion protein of the peptide and the self-assembling protein.

The peptide having the silica synthesis activities may bind to either the N-terminus or the C-terminus, or both of the N-terminus and the C-terminus of a self-assembling protein, or may bind to any one of the N-terminus and the C-terminus of the self-assembling protein via a ligand regardless of binding positions without affecting the innate properties of the peptide. Therefore, the fusion protein according to the present invention refers to all kinds of fusion proteins formed by binding the peptide having the silica synthesis activities to the self-assembling protein regardless of binding positions without affecting the innate properties of the peptide.

In addition to the peptides set forth in SEQ ID NOs: 1 to 7, silaffin R5 (SEQ ID NO: 8), sequence (SEQ ID NO: 9) used for His-Taq, and a sequence (SEQ ID NO: 10) to which silaffin R5 and His-Taq are bound may be used as the peptide having the silica synthesis activities.

The kinds of the self-assembling protein are as described above.

Also, the fusion protein may include a His-Tag sequence(s) at the N-terminus or the C-terminus, or both the N-terminus and the C-terminus in order to enhance expression and purification.

The fusion protein may have an enzyme or a binding peptide, or a heterologous protein such as a fluorescent protein further bound thereto.

The fusion protein may be prepared using methods for synthesizing a peptide, as known in the related art. For example, the fusion protein may be prepared in vitro by a method for synthesizing a peptide using genetic recombination and protein expression systems or a peptide synthesizer.

Therefore, the present invention provides a recombinant vector expressing the fusion protein.

The vector includes a plasmid vector, a cosmid vector, a bacteriophage vector, and a viral vector, but the present invention is not limited thereto. A proper expression vector includes a signal sequence for membrane targeting or secretion, or a leader sequence in addition to a promoter, an operator, an initiation codon, a termination codon, a polyadenylation signal and an enhancer, and may be widely constructed according to a purpose. The promoter of the vector may be constitutive or inducible. Also, the expression vector includes a selective marker for selecting a host cell carrying the vector, and a replicable expression vector may include a replication origin.

According to one exemplary embodiment of the present invention, a recombinant vector is constructed by inserting a ferritin coding gene (SEQ ID NO: 11) according to the present invention and a DNA fragment including a silaffin R5 coding gene (SEQ ID NO: 8) as the peptide for synthesizing silica using a pDuet vector that is a vector for expression in an $E.\ coli$ strain.

The present invention also provides a transformant transduced with a recombinant vector expressing the fusion protein.

The transformation may also include any methods for introducing a nucleic acid into an organism, a cell, a tissue or an organ, and may be performed using a proper standard technique according to a host cell, as known in the related art. Such a method includes electroporation, protoplast fusion, calcium phosphate ($CaPO_4$) precipitation, calcium chloride ($CaCl_2$) precipitation, agitation using silicon carbide fiber, $Agrobacteria$-mediated transformation, PEG, dextran sulfate, and Lipofectamine, but the present invention is not limited thereto.

Also, since levels of expression and modification of a protein vary according to the host cell, the most proper host cell is chosen and used according to a purpose.

The host cells may include procaryotic host cells such as $E.\ coli$, $Bacillus\ subtilis$, $Streptomyces$ sp., $Pseudomonas$ sp., $Proteus\ mirabilis$, or $Staphylococcus$ sp., but the present invention is not limited thereto. Also, lower eucaryotic cells such as fungi (for example, $Aspergillus$ sp., etc.) and yeasts (for example, $Pichia\ pastoris$, $Saccharomyces\ cerevisiae$, $Schizosaccharomyces$ sp., $Neurospora\ crassa$ sp., etc.), and higher eukaryote-derived cells such as insect cells, plant cells, mammalian cells and the like may be used as the host cells.

The transformant may be prepared by introducing the recombinant vector into any host cells. According to one preferred embodiment of the present invention, the transformant may be prepared by introducing a recombinant vector pDuet-R5Pfr into $E.\ coli$ strain BL21(DE3).

The present invention also provides a method for preparing a fusion protein, which includes separating and purifying a culture broth of the transformant transduced with the recombinant vector expressing the fusion protein.

The fusion protein may be purified after the transformant is cultured according to a conventional culture method. An amino acid sequence coding for the fusion protein may be partially modified to the extent which does not affect an activity to produce cytokines according to a base sequence of an insert, that is, a coding gene, introduced into the recombinant vector. The modification refers to a modification caused by deletion, insertion or substitution.

The present invention also provides a polyclonal antibody specifically binding to the fusion protein.

A method for preparing the polyclonal antibody is not particularly limited, but the polyclonal antibody may be prepared according to the following method.

A specific pathogen-free (SPF) animal is injected once to several times with the fusion protein of the present invention to be immunized. Within a predetermined time after the final immunization, whole blood is collected, and serum is extracted from the whole blood to obtain a polyclonal antibody against the protein of the present invention.

The immunized animal is not particularly limited as long as it is an animal used for typical immunization. For example, the immunized animal may be a rat. The number and duration of injections for immunization, and an administration method are not particularly limited since they may be changed or modified at a level of a person having ordinary skill in the art.

The silica fused with the self-assembling protein may be prepared by reacting a silica precursor with the fusion protein so that the fusion protein can be coated with the silica.

The present invention provides a method of synthesizing silica, which includes reacting a silica precursor with at least one peptide selected from the group consisting of amino acid sequences set forth in SEQ ID NOs: 1 to 7, or the fusion protein.

The peptide having the silica synthesis activities according to the present invention may react with the silica precursor in an aqueous solution of weak base, that is, pH 6 to 8, under conditions of normal temperature and normal pressure to synthesize silica.

The method of synthesizing silica according to the present invention will be described in further detail, as follows. A buffer solution of 0.1M $KH_2PO_4$ solution (pH 6 to 8), a silica precursor dissolved in 1 mM HCl solution, and the peptide according to the present invention are mixed at a weight ratio of 0.01 to 1%, and reacted under conditions of normal temperature and normal pressure. Then, the resulting mixture is centrifuged to precipitate the silica.

As described above, the peptide having the silica synthesis activities may be used to synthesize multifunctional silica in an aqueous solution of weak base under the conditions of normal temperature and normal pressure, and thus solve the prior-art problems regarding production of environmentally harmful by-products.

Also, in the method of synthesizing silica according to the present invention, the silica in which the enzyme or the binding peptide is immobilized may be synthesized by allowing the peptide having the silica synthesis activities, the silica precursor and the enzyme or binding peptide to react each other, or by allowing the silica precursor to react with the fusion protein of the enzyme or binding peptide and the peptide having the silica synthesis activities.

In this case, the fusion protein may be coated with the silica, or may be prepared by mixing and reacting the peptide having the silica synthesis activities, the silica precursor and the enzyme or binding peptide at predetermined mixing ratios.

Also, in the method of synthesizing silica according to the present invention, a specific microstructure such as a nanotube or a nanomesh, and a composite silica structure may be formed by allowing the peptide having the silica synthesis activities, the silica precursor and the microstructure to react under the conventional conditions for silica synthesis.

Also, in the method of synthesizing silica according to the present invention, the silica may be prepared in the form of a single silica film by allowing the peptide having the silica synthesis activities, the silica precursor and the microstructure to react under the conventional conditions for silica synthesis so that the fusion protein can be coated with the silica as a single film without forming a precipitate during silica synthesis.

Also, a porous silica may be synthesized through the method of synthesizing silica according to the present invention, which includes allowing the peptide having the silica synthesis activities, the silica precursor and the phospholipid to react with each other to prepare an organic/inorganic complex, and treating the organic/inorganic complex with heat or an organic solvent to remove an organic substance.

Also, in the method of synthesizing silica according to the present invention, an inorganic substance such as hydroxyapatite may be used in addition to the organic substance for silica synthesis to prepare a silica complex.

The silica complex may be obtained by allowing the peptide having the silica synthesis activities, and a silica precursor and the hydroxyapatite to react under the conventional conditions for silica synthesis.

Also, the present invention provides a silica complex in which a surface of a self-assembled structure of at least one peptide selected from the group consisting of amino acid sequences set forth in SEQ ID NOs: 1 to 7 is coated with silica.

The peptide having the silica synthesis activities according to the present invention may be self-assembled, and thus has a spherical self-assembled structure as an autoencapsulation reaction occurs by a reaction for silica synthesis. In this case, a silica complex may be formed by coating a surface of the self-assembled structure with the synthesized silica.

The silica complex may have both of a capsule structure in which void cavities are formed in a composite shell composed of a peptide and silica, and a core-shell structure in which the peptide forms a core region and the silica forms a shell region.

In order to obtain the silica complex having a capsule structure, a peptide may be fused with a spherical self-assembling protein capable of forming a core, for example, a ferritin protein capable of forming spheres having a diameter of approximately 12 nm, or the silica complex having a capsule structure may be obtained by fusing a core-shell polymeric nanosphere with a peptide to form a spherical silica structure and sintering the spherical silica structure.

Also, when a liposome is used as a template, capsule-type hollow silica may be obtained. Also, since the silica spheres themselves may have a core-shell structure formed by means of the peptide, silica spheres may have a core-shell structure in which the peptide forms a core region and the silica forms a shell region.

Therefore, the present invention provides a method for preparing a silica complex, which includes allowing a silica precursor to react with at least one peptide selected from the group consisting of amino acid sequences set forth in SEQ ID NOs: 1 to 7 to prepare a silica complex in which a surface of a self-assembled structure of the peptide is coated with silica through autoencapsulation.

The silica complex may be synthesized by allowing the peptide and the silica precursor to react in an aqueous solution of pH 6 to 8 under conditions of normal temperature and normal pressure.

The kind of the silica precursor is as described above.

Also, the silica complex may further include a fluorescent material, a tissue-specific component, a pharmaceutically active component, an enzyme or a binding peptide, a microstructure, a phospholipid, or hydroxyapatite, which may be directly bound to the N-terminus or the C-terminus, or both of the N-terminus and the C-terminus of the peptide having the silica synthesis activities, or indirectly bound via a chemical, physical covalent or a non-covalent bond or using another medium.

For example, the fluorescent material may include a Dylight 488 NHE-ester dye, Vybrant™ DiI, Vybrant™ DiO, quantum dot nanoparticles, fluorescein, rhodamine, lucifer yellow, B-phycoerythrin, 9-acridine isothiocyanate, lucifer yellow VS, 4-acetamido-4'-isothio-cyanatostilbene-2,2'-disulfonic acid, 7-diethylamino-3-(4'-isothiocyanatophenyl)-4-methylcoumarin, succinimidyl-pyrenebutyrate, a 4-acetamido-4'-isothiocyanatostilbene-2,2'-disulfonic acid derivative, LC™-Red 640, LC™-Red 705, Cy5, Cy5.5, lissamine, isothiocyanate, erythrosine isothiocyanate, diethylenetriamine pentaacetate, 1-dimethylaminonaphthyl-5-sulfonate, 1-anilino-8-naphthalene sulfonate, 2-p-toluidinyl-6-naphthalene sulfonate, 3-phenyl-7-isocyanatocoumarin, 9-isothiocyanatoacridine, acridine orange N-(-p-(2-benzoxazoylyl)phenyl)maleimide thiadiazole, stilbene, pyrene, an Ebene conductor, silica including a fluorescent material, Group II/IV semiconductor quantum dots, Group III/V semiconductor quantum dots, Group IV semiconductor quantum dots, or a mixed structure of multiple components, but the present invention is not particularly limited thereto Preferably, at least one selected from the group consisting of quantum dot nanoparticles, Cy3.5, Cy5, Cy5.5, Cy7, indocyanine green (ICG), Cypate, ITCC, NIR820, NIR2, IRDye78, IRDye80, IRDye82, Cresy Violet, Nile Blue, Oxazine 750, Rhodamine-800, lanthanides, and Texas Red may be used as the fluorescent material, and Group II-VI or III-V compounds may be used as the quantum dot nanoparticles. In this case, at least one selected from the group consisting of CdSe, CdSe/ZnS, CdTe/CdS, CdTe/CdTe, ZnSe/ZnS, ZnTe/ZnSe, PbSe, PbS InAs, InP, InGaP, InGaP/ZnS and HgTe may be used as the quantum dot nanoparticles.

The tissue-specific binding component may be a material which can specifically bind to an antigen, an antibody, RNA, DNA, a hapten, avidin, streptavidin, neutravidin, Protein A, Protein G, lectin, selectin, a radioisotope-labeled component, or a tumor marker, but the present invention is not particularly limited thereto.

The pharmaceutically active component may include siRNA, antisense, an anti-cancer agent, an antibiotic agent, a hormone, a hormone antagonist, an interleukin, an interferon, a growth factor, a tumor necrosis factor, an endotoxin, a lymphotoxin, urokinase, streptokinase, a tissue plasminogen activator, a protease inhibitor, alkylphosphocholine, a component labeled with a radioisotope, a cardiovascular system drug, a gastrointestinal system drug, and a nervous system drug, which may be used alone or in combination, but the present invention is not particularly limited thereto.

The silica complex according to the present invention may have an enzyme or a binding peptide immobilized therein, and thus may be used as a biosensor used to detect a certain component such as a nucleic acid, a protein, a polysaccharide or a pathogen through a color reaction, a fluorescence reaction, a luminescence reaction, an electrochemical reaction, and the like.

The kind of the enzyme or the binding peptide is as described above.

The silica complex according to the present invention may form a composite structure by using its self-assembling structure with a certain microstructure such as a nanotube or a nanomesh.

When the phospholipid is included in the silica complex, the silica organic/inorganic complex may be formed, or a porous silica structure may be formed during removal of an organic substance.

When the hydroxyapatite is included in the silica complex, a silica-based complex may be formed with an inorganic substance.

Therefore, the silica complex of the present invention having various functional components bound thereto may be used for a drug delivery system, a biosensor for detecting a nucleic acid, a protein, a polysaccharide or a pathogen, a bone substitute, a cell culture coating agent, a 3D scaffold, a contrast agent, a diagnostic probe, a functional fiber, a filter, and the like.

Also, the present invention relates to a silica complex in which a surface of a self-assembled structure of at least one peptide selected from the group consisting of amino acid sequences set forth in SEQ ID NOs: 1 to 10, or a self-assembling protein is coated with silica.

When the self-assembling protein is a fusion protein bound to the peptide having silica synthesis activities, the self-assembling protein may form a self-assembled structure with a core-shell structure through a reaction of the silica precursor with the fusion protein, and silica may be synthesized from the silica precursor by means of the peptide having silica synthesis activities which is bound to the structure using the self-assembled structure as a template, thereby synthesizing a structure in which a surface of the self-assembled structure is coated with silica.

The kind of the self-assembling protein is as described above.

The self-assembling protein may further include metal ions, an isotope, a fluorescent material, a tissue-specific component, a pharmaceutically active component, an enzyme or a binding peptide, a nanotube, or a nanomesh, which may be directly or indirectly bound to the N-terminus or the C-terminus, or both of the N-terminus and the C-terminus of the self-assembling protein via a chemical, physical covalent or a non-covalent bond or using another medium.

The metal ions may include iron, manganese, copper or cobalt ions, or alloys thereof, but the present invention is not particularly limited thereto.

The present invention relates to a drug delivery system including the silica complex, and a pharmaceutically acceptable carrier.

The silica complex according to the present invention has a core-shell structure, and thus is especially suitable for delivering a pharmaceutically active component as described above.

The pharmaceutically acceptable carrier includes a carrier and a vehicle generally used in the field of medicine. More particularly, the pharmaceutically acceptable carrier includes an ion exchange resin, alumina, aluminum stearate, lecithin, a serum protein (for example, human serum albumin), a buffering substance (for example, various phosphates, glycine, sorbic acid, calcium sorbate, a partial glyceride mixture with saturated vegetable fatty acid), water, a salt or electrolyte (for example, protamine sulfate, sodium dihydrogen phosphate, potassium hydrogen phosphate, sodium chloride, and a zinc salt), colloidal silica, magnesium trisilicate, polyvinylpyrrolidone, cellulose-based substrate, polyethylene glycol, sodium carboxymethyl cellulose, polyarylate, wax, polyethylene glycol, or wool fat, but the present invention is not limited thereto.

Also, the drug delivery system according to the present invention may further include a lubricant, a wetting agent, an emulsifying agent, a suspending agent, or a preservative in addition to the above-described components.

In one aspect, the drug delivery system according to the present invention may be prepared in a water-soluble solution for parenteral administration. Preferably, a buffering solution such as a Hank's solution, a Ringer's solution, or physically buffered saline may be used. A substrate which can increase viscosity of a water-soluble injection suspension, such as sodium carboxymethyl cellulose, sorbitol, or dextran, may be added to the suspension.

Another preferred aspect of the drug delivery system according to the present invention may be in the form of a sterile injectable preparation such as a sterile injectable aqueous or oily suspension. Such a suspension may be formulated according to a technique known in the related art using a proper dispersing or wetting agent (for example, Tween 80), and a suspending agent.

Also, the sterile injectable preparation may be a sterile injectable solution or suspension in a nontoxic, parenterally available diluent or solvent (for example, a solution in 1,3-butanediol). The vehicle and solvent which may be used herein includes mannitol, water, a Ringer's solution, and an isotonic sodium chloride solution. In addition, sterile nonvolatile oil may be typically used as a solvent or a suspending medium. For this purpose, any of less pungent nonvolatile oils may be used since they include synthetic mono- or di-glyceride.

A proper dosage of the drug delivery system according to the present invention may be widely adjusted according to the factors such as a method of formulation, a mode of administration, age, body weight, sex, and health condition of a patient, diet, an administration time, a route of administration, an excretion rate, and sensitivity to a reaction.

Also, the present invention relates to a contrast agent composition including the silica complex, and a pharmaceutically acceptable carrier.

The silica complex according to the present invention may be used as a contrast agent capable of imaging a target part using a magnetic-resonance and optical imaging system since a fluorescent material is physicochemically bound to the silica complex.

When the contrast agent composition according to the present invention is administered into tissues or cells separated from a target to be diagnosed, the contrast agent composition may be used to detect a signal emitted by a fluorescent silica complex to obtain an image.

In this case, a magnetic resonance imaging system (MRI) and an optical imaging system may be preferably used to detect the signal emitted from the fluorescent silica complex.

The magnetic resonance imaging system is a device for imaging a biological tissue by putting the biological tissue in the strong magnetic field, irradiating the biological tissue with specific frequency waves so that the atomic nuclei such as hydrogen present in the biological tissue can absorb energy to be in a high energy state, suspending the wave irradiation to emit the energy of the atomic nuclei such as hydrogen, converting the energy into signals, and imaging the signals processed with a computer. Since magnetism or waves are hindered by bones, clear 3D tomographic images may be obtained for tumors in the surroundings of the hard skulls, or brains or bone marrows at any angles in a vertical or horizontal direction. In particular, the magnetic resonance imaging system may be a T2 spin-spin relaxation magnetic resonance imaging system.

Also, the present invention relates to a target-directed contrast agent composition including the silica complex, and a pharmaceutically acceptable carrier.

The silica complex according to the present invention may exhibit fluorescence since a fluorescent material is bound to the silica complex. Also, the silica complex may be targetable since a tissue-specific binding component may bind to the silica complex. As a result, the silica complex according to the present invention may be used as a contrast agent capable of imaging a target site using a magnetic-resonance and optical imaging system.

In addition, the present invention is directed to a contrast agent composition for simultaneous diagnosis or treatment, which includes the silica complex, and a pharmaceutically acceptable carrier.

The silica complex according to the present invention may exhibit fluorescence since a fluorescent material is bound to the silica complex. At the same time, since the silica complex according to the present invention physicochemically binds to a pharmaceutically active component, the silica complex may be used as a nanoprobe and a drug for separation, diagnosis, or treatment of biological molecules by means of a magnetic-resonance and optical imaging system, or used as a gene delivery vehicle.

One representative example of the in vivo diagnosis using the silica complex may include a molecular magnetic resonance imaging or magnetic relaxation sensor. As the silica complex increases in size, the silica complex shows a higher T2 contrast effect. Using this property, the silica complex may be used as a sensor for detecting biological molecules. That is, when entanglement of the peptide having silica synthesis activities is induced by certain biological molecules, a T2 magnetic resonance imaging effect is improved accordingly. This difference may be used to detect the biological molecules.

Also, the silica complex according to the present invention may be used to diagnose and/or treat arteriosclerosis, or various diseases associated with a tumor, for example, gastric cancer, lung cancer, breast cancer, ovarian cancer, liver cancer, bronchogenic cancer, nasopharyngeal cancer, laryngeal cancer, pancreatic cancer, bladder cancer, colon cancer, and cervical cancer.

More particularly, the tumor cells expressing and/or secreting a specific substance which is hardly or never produced in normal cells is generally named a "tumor marker." When a substance capable of specifically binding to such a tumor marker is bound to the silica complex, the silica complex may be effectively used for tumor diagnosis. Various tumor markers as well as substances capable of specifically binding to the tumor markers are known in the related art.

Also, the tumor markers may be divided into a ligand, antigen, receptor, and nucleic acids encoding the ligand, the antigen, and the receptor, depending on an action mechanism.

When the tumor marker is a "ligand," a substance capable of specifically binding to the ligand may be introduced into the silica complex according to the present invention. In this case, a receptor or an antibody capable of specifically binding to the ligand may be used properly. Examples of the ligand that may be used in the present invention and the receptor capable of specifically binding to the ligand include C2 of synaptotagmin and phosphatidyl serine, annexin V and phosphatidyl serine, integrin and a receptor thereof, a vascular endothelial growth factor (VEGF) and a receptor thereof, angiopoietin and a Tie2 receptor thereof, somatostatin and a receptor thereof, and a vasointestinal peptide and a receptor thereof, but the present invention is not particularly limited thereto.

Representative examples of the "receptor" which is the tumor marker include a folic acid receptor expressed in ovarian cancer cells. A substance capable of specifically binding to the receptor (folic acid in the case of a folic acid receptor) may be introduced into the silica complex according to the present invention. In this case, a ligand or an antibody capable of specifically binding to the receptor may be used properly.

When the tumor marker is an "antigen," a substance capable of specifically binding to the antigen may be introduced into the silica complex according to the present invention. In this case, an antibody capable of specifically binding to the antigen may be used properly. Examples of the antigen that may be used in the present invention and the antibody specifically binding to the antigen may include a carcinoembryonic antigen (a colon cancer marker antigen) and Herceptin (Genentech, USA), a HER2/neu antigen (breast cancer marker antigen) and Herceptin, and a prostate-specific membrane antigen (a prostate cancer marker antigen) and Rituxan (IDCE/Genentech, USA).

Such an antibody may be commercially available, or may be prepared according to the methods known in the related art. In general, a mammal (for example, a mouse, a rat, a goat, a rabbit, a horse, or a sheep) is immunized once or more with a proper amount of an antigen. When a titer reaches a proper level within a predetermined period of time, the antibody is recovered from a serum of the mammal. The recovered antibody may be optionally purified using a known process, and stored in a frozen buffered solution for future use. The details of this method are widely known in the related art.

Meanwhile, the "nucleic acid" includes RNA and DNA, which encode the ligand, the antigen, the receptor, or a fragment thereof as described above. Since the nucleic acid has a characteristic of forming base pairs between complementary sequences as known in the related art, the nucleic acid having a specific base sequence may be detected using a nucleic acid having a base sequence complementary to the base sequence. The nucleic acid having a base sequence complementary to the nucleic acid encoding the enzyme, the ligand, the antigen, or the receptor may be introduced into the silica complex according to the present invention.

Also, the nucleic acid may be effectively used to bind to the silica complex since a functional group such as —$NH_2$, —SH, or —COOH is bound to the 5' and 3' termini of the nucleic acid.

Such a nucleic acid may be synthesized using a standard method known in the related art, for example, an automated DNA peptide synthesizer (for example, a DNA peptide synthesizer commercially available from Biosearch Technologies, Applied BioSystem, and the like). By way of example, a phosphorothioate oligonucleotide may be synthesized using a method disclosed in Stein et al. *Nucl. Acids Res.* 1988, vol. 16, p. 3209. A methylphosphonate oligonucleotide may be prepared using a controlled glass polymer support (Sarin et al. *Proc. Natl. Acad. Sci. U.S.A.* 1988, vol. 85, p. 7448).

Additionally, the present invention is directed to a multi-diagnostic probe including the silica complex, and a diagnostic probe.

A probe for diagnosing a T1 magnetic resonance image, an optical diagnostic probe, a CT diagnostic probe, or radioisotope may be used as the diagnostic probe.

For example, the multi-diagnostic probe may be used to perform diagnosis of a T2 magnetic resonance image and a T1 magnetic resonance image at the same time when the probe for diagnosing a T1 magnetic resonance image is bound to the silica complex, perform diagnosis of a magnetic resonance image and an optical image at the same time when the optical diagnostic probe is bound to the silica complex, and perform diagnosis of a magnetic resonance image and a CT diagnostic image at the same time when the CT diagnostic probe is bound to the silica complex. Also, the multi-diagnostic probe may be used to perform diagnosis of a magnetic resonance image, PET and SPECT at the same time when the radioisotope binds to the silica complex.

In this case, the probe for diagnosing a T1 magnetic resonance image includes a Gd compound or an Mn compound, the optical diagnostic probe includes an organic fluorescent dye, quantum dots, or a dye-labeled inorganic support (for example, $SiO_2$, or $Al_2O_3$), the CT diagnostic probe includes an iodine (I) compound or gold nanoparticles, and the radioisotope includes In, Tc, or F.

Also, the present invention is directed to a fiber or filter into which the silica complex is electrospun.

The silica complex according to the present invention may be used to prepare various filters and functional fibers when a structure such as a fibrous bio-silica is formed using an electrospinning method.

Also, when a peptide and a functional protein may be fused using a genetic engineering method, and the resulting fusion protein is electrospun, it is possible to prepare a fiber having functionalities.

Also, the present invention is directed to use as a bone substitute, a tooth substitute, a cell culture coating agent in a medium for bone cell differentiation and a 3D scaffold material, all of which include the silica complex.

When the silica complex according to the present invention include hydroxyapatite, the silica complex may be used as a bone substitute, a tooth substitute, a cell culture coating agent in a medium for bone cell differentiation and a 3D scaffold material through formation of the silica-based complex.

In addition, the present invention is directed to a photonic device including the silica complex.

The silica complex according to the present invention may be adsorbed onto a surface of a semiconductor substrate to form a nanoscaled bio-silica, and thus may be used for photonic devices.

Furthermore, the present invention is directed to a biosensor for detecting biomolecules, which includes the silica complex.

The silica complex according to the present invention may be used to detect biomolecules such as nucleic acids, proteins, polysaccharides, or pathogens since an enzyme or a binding peptide may be immobilized in the silica complex.

Example 1

Searching for Peptides for Synthesizing Silica Derived from Marine Species

It was assumed that there were various amino acid sequences which could synthesize silica from a variety of marine species and searched for novel peptides for synthesizing silica from the NCBI's protein database in the U.S. Using peptides having amino acid sequences in which amino acids containing a hydroxyl group (—OH) and an amine group (—$NH_2$), both of which play an important role in post-translation modification, such as serine, lysine, arginine and histidine, were present at high contents, as queries (blast.ncbi.nlm.nih.gov). The proteins produced from the marine species among the searched proteins were screened, and 7 peptides having an amino acid sequence expected to have the probability of synthesizing silica present in the protein were selected (see Table 1).

TABLE 1

Sequences and Origins of Peptides

| SEQ ID NO. | Name | Amino acid sequence | Origins |
|---|---|---|---|
| 1 | RG | RRRRRGCGRRRGGRG GRGRGGCGRRR | CAMK/TSSK protein kinase from *Salpingoeca* sp.ATCC50818 Accession No. EGD72728 amino acid 294 to 319 |

TABLE 1-continued

Sequences and Origins of Peptides

| SEQ ID NO. | Name | Amino acid sequence | Origins |
|---|---|---|---|
| 2 | Sal_p1 | CGRRRGGRGGRGRGG CGRRR | CAMK/TSSK protein kinase from *Salpingoeca* sp.ATCC50818 Accession No. EGD72728 amino acid 300 to 319 |
| 3 | Ect_p1 | SSRSSSHRRHDHHDH RRGS | Hypothetical protein Esi_0050_0074 from *Ectocarpus siliculosus* Accession No. CBJ26926 amino acid 2833 to 2851 |
| 4 | Ect_p2 | SSKKSGERHHRSA | Hypothetical protein Esi_0050_0074 from *Ectocarpus siliculosus* Accession No. CBJ26926 amino acid 1674 to 1686 |
| 5 | Vol_p1 | SGRRRGSRRRGSRRR | Hypothetical protein VOLCADRAFT_33984 from *Volvox carteri f. nagariensis* Accession No. XP_002959480 Amino acid 10 to 24 |
| 6 | Vol_p2 | SRLRGRRRRLSPGR | Hypothetical protein VOLCADRAFT_95499 from *Volvox carteri f. nagariensis* Accession No. XP_002954619 Amino acid 461 to 474 |
| 7 | Vol_p3 | SSHRHHHDHHDHHH | Hypothetical protein VOLCADRAFT_95499 from *Volvox carteri f. nagariensis* Accession No. XP_002954619 Amino acid 630 to 643 |

A No. 1 peptide (SEQ ID NO: 1) had a sequence of $294^{th}$ to $319^{th}$ amino acids selected from an amino acid sequence of CAMK/TSSK protein kinase from *Salpingoeca* sp. ATCC 50818 belonging to a family of flagellates, and named "RG." A No. 2 peptide (SEQ ID NO: 2) had a sequence of $300^{th}$ to $319^{th}$ amino acids selected from the amino acid sequence, a length of which was reduced from that of the RG, and named "Sal_p1." A No. 3 peptide (SEQ ID NO: 3) had a sequence of $2,833^{rd}$ to $2,851^{st}$ amino acids selected from an amino acid sequence of a protein (Genebank Accession No. CBJ26926) which was derived from a brown algae, *Ectocarpus siliculosus*, and whose functions were not known, and named "Ect_p1," and a No. 4 peptide (SEQ ID NO: 4) had a sequence of $1,674^{th}$ to $1,686^{th}$ amino acids selected from the amino acid sequence of the same protein, and named "Ect_p2." A No. 5 peptide (SEQ ID NO: 5) had a sequence of $10^{th}$ to $24^{th}$ amino acids selected from an amino acid sequence of a protein (Genebank Accession No. XP_002959480) which was derived from *Volvox* sp. and whose functions were not known, and named "Vol_p1." No. 6 and No. 7 peptides (SEQ ID NOs: 6 and 7) had sequences of $461^{st}$ to $474^{th}$ and $630^{th}$ to $643^{rd}$ amino acids selected from an amino acid sequence of a protein (Genebank Accession No. XP_002954619) which were derived from *Volvox* sp. and whose functions were not known, and named "Vol_p2" and "Vol_p3," respectively.

The 7 peptides were requested to be synthesized by Peptron Co. (Daejeon, Korea) to obtain synthetic peptides with a purity of 90%. The theoretical characteristics of the synthesized peptides were analyzed using a PepDraw program (http://www.tulane.edu/~biochem/WW/PepDraw/index.html), and listed in the following Table 2.

TABLE 2

Basic Characteristics of Peptides

| Name | Length (a.a) | Molecular Weight | Isoelectric Point | Total Charges | Hydrophobicity |
|---|---|---|---|---|---|
| RG | 26 | 2979.6553 | 13.05 | +14 | +44.70 Kcal * mol$^{-1}$ |
| Sal_p1 | 20 | 2142.1294 | 12.79 | +9 | +34.5 Kcal * mol$^{-1}$ |
| Ect_p1 | 19 | 2297.1066 | 12.31 | +3 | +39.79 Kcal * mol$^{-1}$ |
| Ect_p2 | 13 | 1467.7633 | 11.54 | +3 | +28.9 Kcal * mol$^{-1}$ |
| Vol_p1 | 15 | 1722.0436 | 13.39 | +9 | +29.02 Kcal * mol$^{-1}$ |
| Vol_p2 | 14 | 2921.6813 | 13.26 | +7 | +21.43 Kcal * mol$^{-1}$ |
| Vol_p3 | 14 | 1815.7892 | 6.95 | 0 | +38.88 Kcal * mol$^{-1}$ |

Example 2

Examination of Silica Synthesis Activities According to Kinds of Peptides Capable of Synthesizing Silica To determine whether the synthesized peptides had silica synthesis activities, the synthesized peptides were dissolved in deionized distilled water so that the synthesized peptides were present at a concentration of 2.5 to 5 mg/mL, and then examined for silica synthesis activities using a method proposed in the articles by Luckarift et al. (Luckarift et al., 2004, *Nat Biotechnol* 22: pp. 211-213). A silaffin R5 peptide (SSKKSGSYSGSKGSKRRIL: SEQ ID NO: 8) was used as the control.

Specific description of an experimental method was as follows. 80 µl of a 0.1 M $KH_2PO_4$ buffer solution whose pH was adjusted to pH 8 using 0.1 M NaOH, 10 µl of a 1 M solution of tetramethyl orthosilicate (TMOS) which was a silicone monomer dissolved in a 1 mM HCl solution, and 10

μl of a 25 mg/mL peptide solution were mixed, reacted at normal temperature for 5 minutes, and then centrifuged at 14,000 g for 10 seconds to precipitate the synthesized silica. The resulting precipitate was washed with alcohol twice and washed with distilled water twice, and dried in the air. For quantitative analysis, the dried silica precipitate was added to a 1M NaOH solution, and reacted at 95° C. for 30 minutes to be decomposed, thereby inducing a color reaction using a principle that a yellow reaction product was formed through a reaction of silica with molybdate. The solutions used in this reaction were a solution of 2% ammonium molybdate (Sol A) and a solution of 5% oxalic acid (Sol B) dissolved in 1 M hydrochloric acid solution and 0.1 N sulfuric acid solution, and a Sol C solution obtained by mixing a solution of 200 mM ascorbic acid dissolved in 10% acetone and a solution of 0.6% sodium dodecyl sulfate (SDS) at a mixing ratio of 1:1. Referring to the functions of the respective solutions, first, HCl was added to neutralize silica hydrolyzed with NaOH. Second, Sol A that was molybdate solution used to develop a color of the silica was added and reacted for 5 minutes, and the oxalic acid solution, Sol B, was added to prevent binding of molybdate to a phosphate group. Finally, when Sol C was added thereto, ascorbic acid served to enhance color intensity by reducing a complex of silica and molybdate to facilitate a color change from yellow to blue.

Using the fact that a concentration of silica was proportional to the color intensity, the concentration of the synthesized silica was calculated by reading absorbance at 700 nm.

Figure 2:
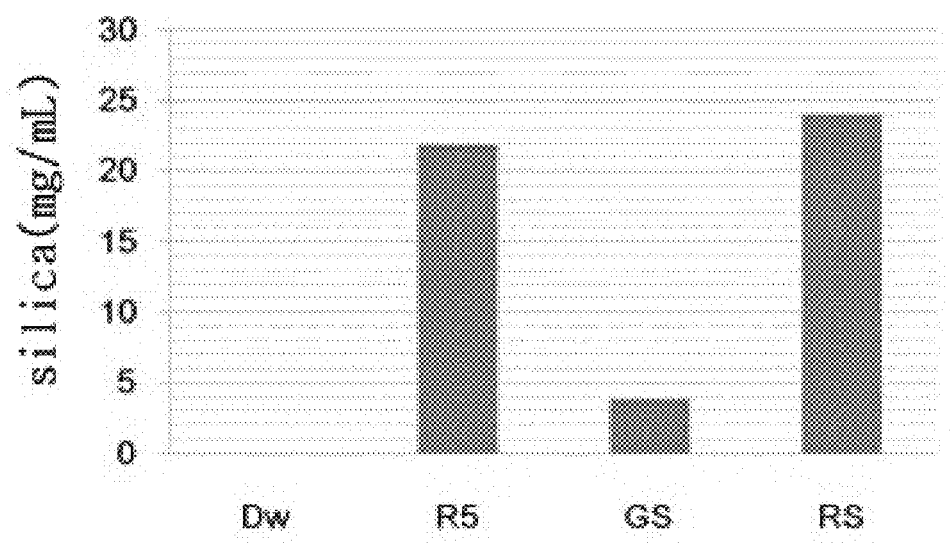
FIG. 2 is a graph showing the results obtained by quantifying the results of silica synthesis by the marine species-derived peptides capable of synthesizing silica, that is, R5, GS and RG peptides, according to the present invention.

Like the R5 peptide used as the control, as soon as the No. 1 RG peptide was added, a silica precipitation reaction appeared. When a GS peptide (GSSSSGSSSSSNNK: SEQ ID NO: 13) rich in serine residues was added as another synthetic peptide, a precipitation reaction was not observed (FIGS. 1 and 2).

Next, 6 peptides in which the number of amino acids was reduced to enhance solubility, compared to the RG peptide, were further synthesized, and the silica synthesis activities of the peptides were compared to those of the RG peptide.

Figure 3:
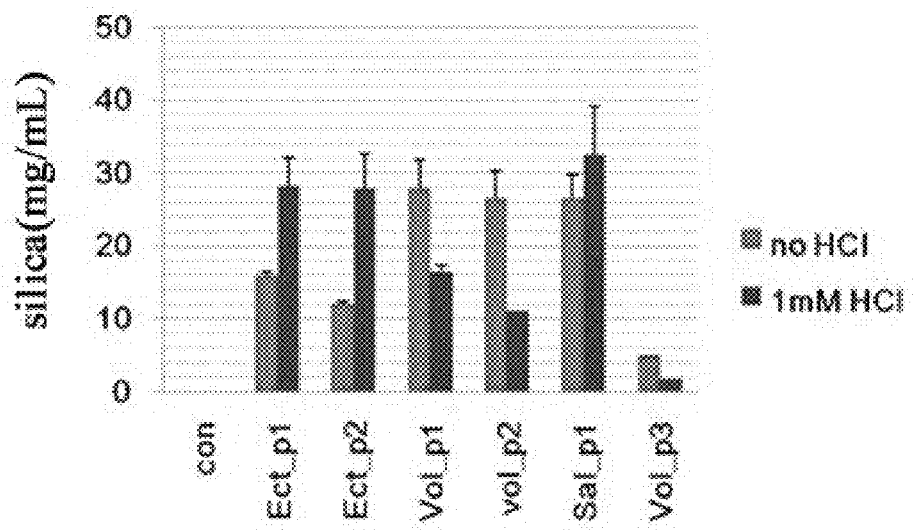
FIG. 3 is a graph showing the results obtained by quantifying the results of silica synthesis according to the kind of peptides derived from the marine species-derived peptide RG capable of synthesizing silica according to the present invention.

As shown in FIG. 3, it was revealed that the Ect_p1, Ect_p2 and Sal_p1 showed an increased synthetic rate of silica when a substrate was activated with silicic acid in a 1 mM HCl solution, but the Vol_p1 and Vol_p2 showed a decreased synthetic rate of silica when the substrate was rather converted into silicic acid.

The silica synthesis activities according to the kinds of the peptides were characteristic in consideration of the pH stability and activities of an organic substance for use to coat silica and immobilize an enzyme, and thus were expected to use the peptides for synthesizing silica.

Figure 4:
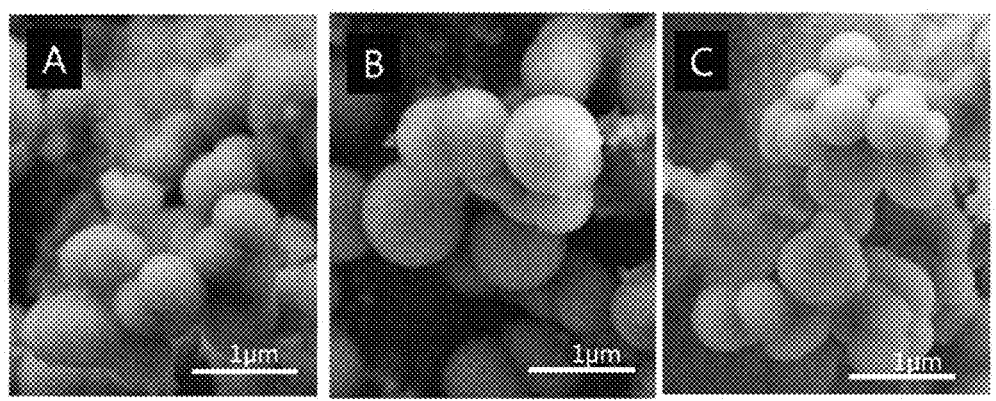
FIG. 4 is a scanning electron microscope image showing the shapes of the silica precipitates formed by the peptides EctP1, SalP1 and VolP2 according to the present invention: (A) shows the shape of silica synthesized by EctP1 at pH 7, (B) shows the shape of silica synthesized by SalP1 at pH 7, and (C) shows the shape of silica synthesized by VolP2. The size of a scale bar indicated in FIG. 4 is 1 μm.

FIG. 4 is a scanning electron microscope image showing the shapes of the silica precipitates formed by the peptides EctP1, SalP1 and VolP2 according to the present invention. In the silica synthesis using the peptides, the reaction easily occurred at pH 6 to 8, and the spherical silica organizers formed by the peptides has a small diameter of 200 to 300 nm or a high diameter of 1 μm or more.

Example 3

Fusion of Useful Protein with Peptide Using Genetic Engineering Method

Figure 5:
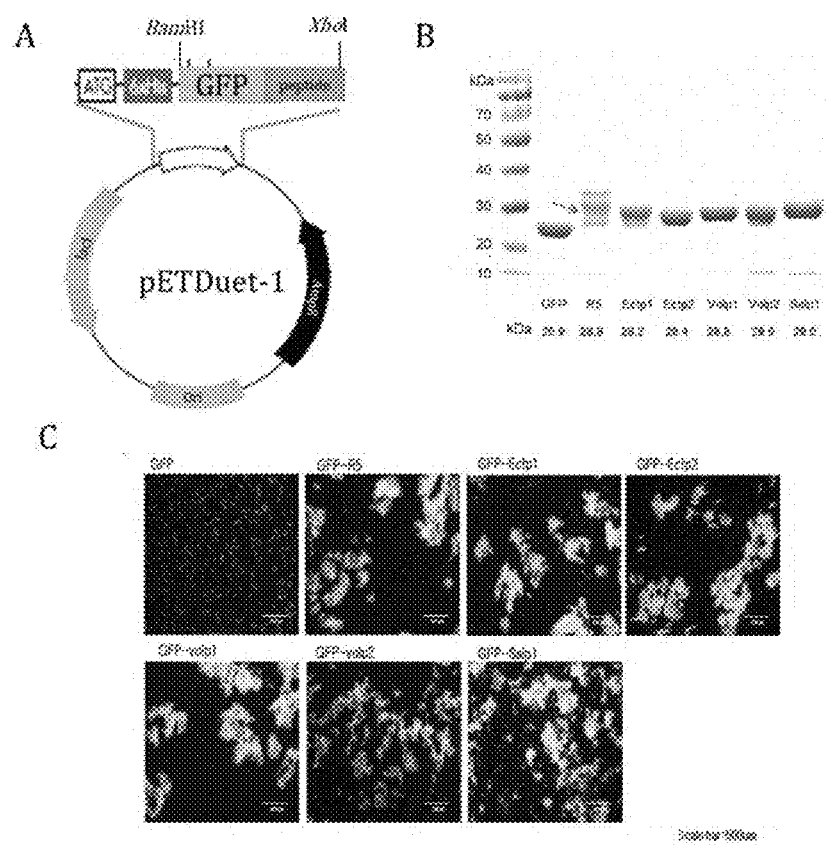
FIG. 5 shows (A) a map of a vector for producing a protein in which a green fluorescent protein is fused with the respective peptides according to the present invention, (B) the SDS-PAGE electrophoresis results of the proteins produced by the vector, and (C) fluorescence microscope images in silica-forming reactions by means of the proteins. The size of a scale bar indicated in FIG. 5 is 500 μm.

Since the peptide for synthesizing silica was able to be fused with various useful proteins using a genetic engineering method, it was possible to visually determine an expression level, activities and locations of the proteins. Therefore, a fusion of a peptide with a biosensor and GFP used as a various tag were performed, and a schematic view of an expression vector was shown in FIG. 5A. The expressed proteins were confirmed using SDS-PAGE (FIG. 5B).

Figure 6:
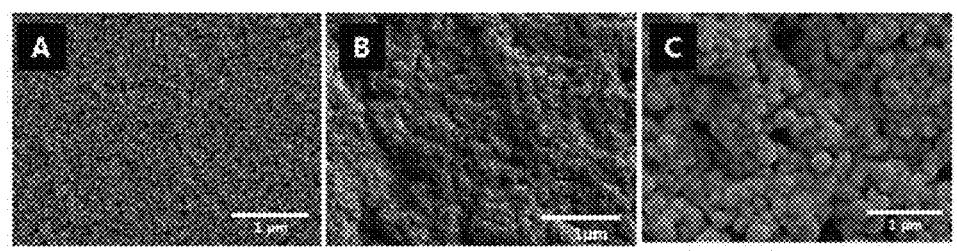
FIG. 6 shows scanning microscope images of a silica structure synthesized by a protein in which a green fluorescent protein is fused with the peptide (SalP1) according to the present invention: (A) shows silica structure non-specifically formed without a protein or peptide, (B) shows silica structure formed in the presence of only a green fluorescent protein, and (C) shows a silica structure formed by a protein with which the peptide SalP1 and a green fluorescent protein are genetically fused.

A reaction for silica synthesis was performed, as follows. 10 μl of a 1 M solution of TMOS that is a silica precursor dissolved in a 1 mM HCl solution was mixed in an Eppendorf tube with 90 μl of a 0.1 M $NaH_2PO_4$ buffer solution containing 1 to 10 μg of the fusion protein, reacted at normal temperature for 5 minutes, and then centrifuged at 14,000 g for 30 seconds to precipitate the synthesized silica. Fluorescence microscope images of the fusion proteins of GFP and peptide coated with silica through autoencapsulation are shown in FIG. 5C. Scanning microscope images of the fusion proteins of GFP and SalP1 coated with silica through autoencapsulation are shown in FIG. 6C. In this case, the spherical structures having a uniform size of approximately 200 nm were formed, compared to the silica precipitate formed by the non-specifically formed silica (A) and the GFP (B).

Figure 7:
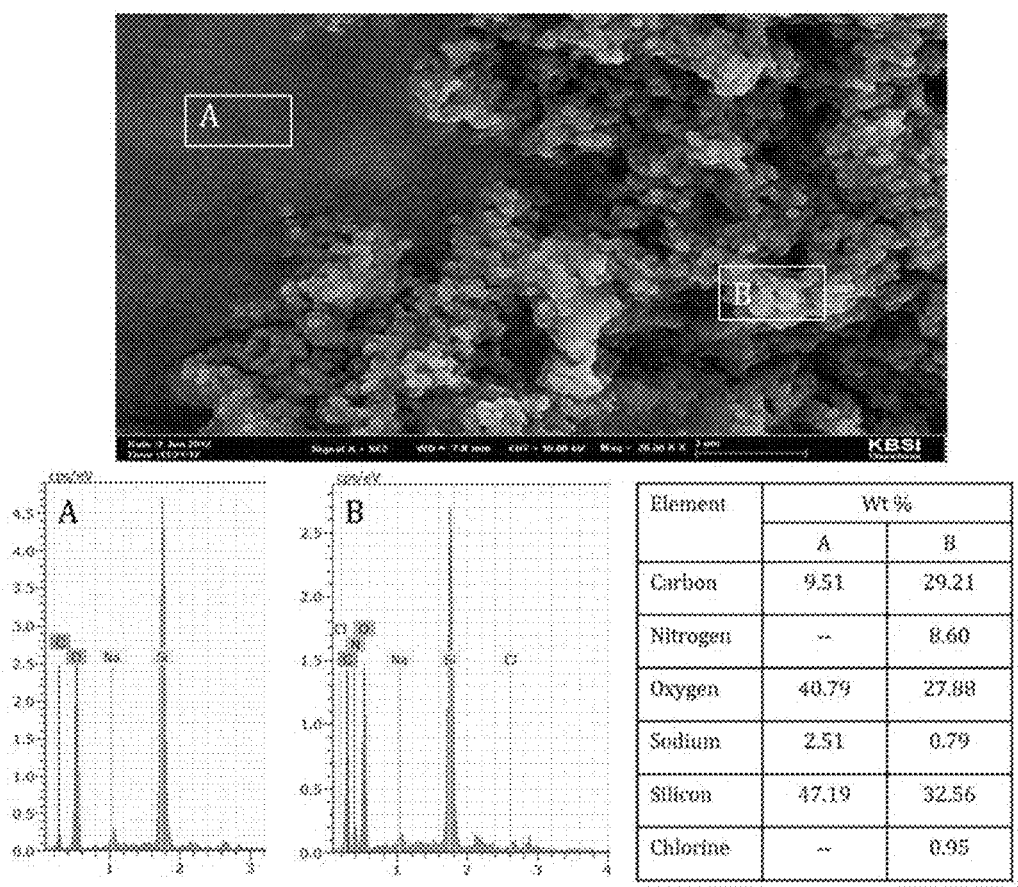
FIG. 7 is a diagram showing the analysis of components of a silica structure, as measured using an energy dispersive X-ray spectrometer (EDX): The dispersive X-ray spectrometry results of (A) a region of non-specifically precipitated silica and (B) a region of silica structure synthesized by GFP-SalP1.

The components of silica formed by GFP-SalP1 were analyzed using an energy dispersive X-ray spectrometer (EDX). As a result, a nitrogen component was detected in a zone of the spherical silica structure, whereas the nitrogen component was not detected in a zone of the non-specifically precipitated silica (FIG. 7). From these facts, it could be seen that the spherical silica structures having a uniform size were formed by the GFP-SalP1.

As a result, it was possible to immobilize a variety of functional proteins in beads, surfaces or certain structures by means of autoencapsulation using genetically engineered fusions with the peptides for synthesizing silica.

Example 4

Preparation of Silaffin R5-Ferritin Fusion Protein (Pfr Cloning)

A pfr gene (SEQ ID NO: 11) was amplified through PCR using a forward sequence (5'-cgggatccgATGTTATCAAAA-GACATCATTAAGTTGCTA-3'; PF: SEQ ID NO: 14) and a reverse sequence (5'-ccgCTCGAGTCATTAAGATTTCCT-GCTTTTAGCGATC-3'; PR: SEQ ID NO: 15) derived from *H. pylori* 26695 DNA, digested with restriction enzymes BamHI and XhoI, and added to a pDuet vector digested with the same restriction enzymes to construct an expression vector pDuet-Pfr (FIGS. 8 and 9).

(Preparation of Silaffin R5-Ferritin)

Silaffin R5-ferritin was obtained by binding silaffin R5 to the N-terminus of ferritin, and cloned into a vector for expression. More particularly, primary PCR was performed using a ferritin expression vector pDuet-Pfr as a template, and 5'-CAGCAAAGGCAGCAAACGCCGCATTCT-GTTATCAAAAGACATCATTAAGTTGCTA-3' (SPF: SEQ ID NO: 16) and PR, and secondary PCR was performed using the amplified PCR product as a template, and 5'-cgggatc-cGAGCAGCAAAAAAAGCGGCAGCTAT-AGCGGCAGCAAAGGCAGCAAACG CCGCATTCTG-3' (SF: SEQ ID NO: 17) and PR to obtain a gene in which the silaffin R5 was bound to the ferritin. The gene was digested with BamHI and XhoI, and cloned into the pDuet vector digested with the same restriction enzymes to obtain a final expression vector pDuet-R5Pfr (FIG. 10).

(Expression of His Tag-Free Pfr)

The silica synthesis activities of the His-tagged silaffin R5-ferritin was measured using His-tagged ferritin as the control. As a result, both the silaffin R5-ferritin and the His-tagged ferritin showed the silica synthesis activities.

Based on these results, expression of the His tag-free ferritin was carried out to determine whether a His-tag sequence itself or ferritin showed the silica synthesis activities.

When a pfr gene was intended to be inserted between NcoI and XhoI sites of the pDuet vector, the pDuet vector was digested with NcoI and XhoI due to the presence of an NcoI site within the pfr gene, and the pfr gene was obtained by inserting a BsaI site capable of providing an NcoI site to a 5'-terminal sequence of a forward primer for pfr amplification, and digested with BsaI, thereby forming the NcoI site in the pfr gene (5'-gcccctctcggtctcccATGTTAT-CAAAAGACATCAT TAAGTT-3'; BsaI_PF: SEQ ID NO: 18). The pfr gene was amplified using BsaI_PF and PR, and cloned into a vector digested with BsaI and XhoI to prepare a His tag-free Pfr expression vector (FIG. 11).

(Transformation for Expression of Recombinant Ferritin)

*E. coli* BL21(DE3) containing a T7 RNA polymerase gene was transformed with each production vector to ensure a ferritin-producing strain.

(Production of Recombinant Ferritin)

*E. coli* BL21(DE3) colony containing the ferritin-producing vector was seeded in 3 mL of LB liquid medium supplemented with 50 μg/mL of ampicillin, and then incubated at 37° C. Thereafter, 0.1 mL of a strain culture broth in a log phase seeded in 50 mL of an LB medium (1.0% tryptone, 0.5% yeast extract, and 1% NaCl), and incubated at 37° C. and 200 rpm for 4 hours. Subsequently, IPTG was added to the resulting culture broth so that IPTG was present at a final concentration of 0.1 mM so as to induce expression of the target protein.

After addition of IPTG, the culture broth was additionally incubated at 37° C. for 3 hours, and then centrifuged at 4° C. and 4,000 rpm for 20 minutes to collect the strain. Thereafter, the strain was suspended with a buffer solution (a 20 mM phosphate buffer solution (pH 8.0) supplemented with 0.3 M NaCl and 1 mM PMSF), treated with 0.5 mg/mL of a lysozyme, and then reacted at normal temperature for 30 minutes. Then, the resulting culture broth was repeatedly frozen and thawed three times (−70° C./37° C.).

The resulting strain was homogenized by repeatedly sonicating the strain at 40 W for 10 seconds three times (left on ice for 10 seconds per sonication), and centrifuged at 12,000 rpm for 10 minutes to collect a supernatant. The ferritin in which the His-tagged ferritin was bound to R5 was subjected to cobalt affinity column chromatography (using a talone resin commercially available from Clone Tech) equilibrated with a 20 mM phosphate buffer solution (pH 8) containing NaCl at a final concentration of 0.3 M, and a recombinant ferritin protein having 6 histidine residues tagged at the N-terminal region thereof was eluted with 150 mM imidazole. The strain was homogenized, and centrifuged to obtain a supernatant. Then, the supernatant was subjected to SDS-PAGE and Western blotting so as to determine an expression level and molecular weight of each recombinant ferritin.

Figure 12:
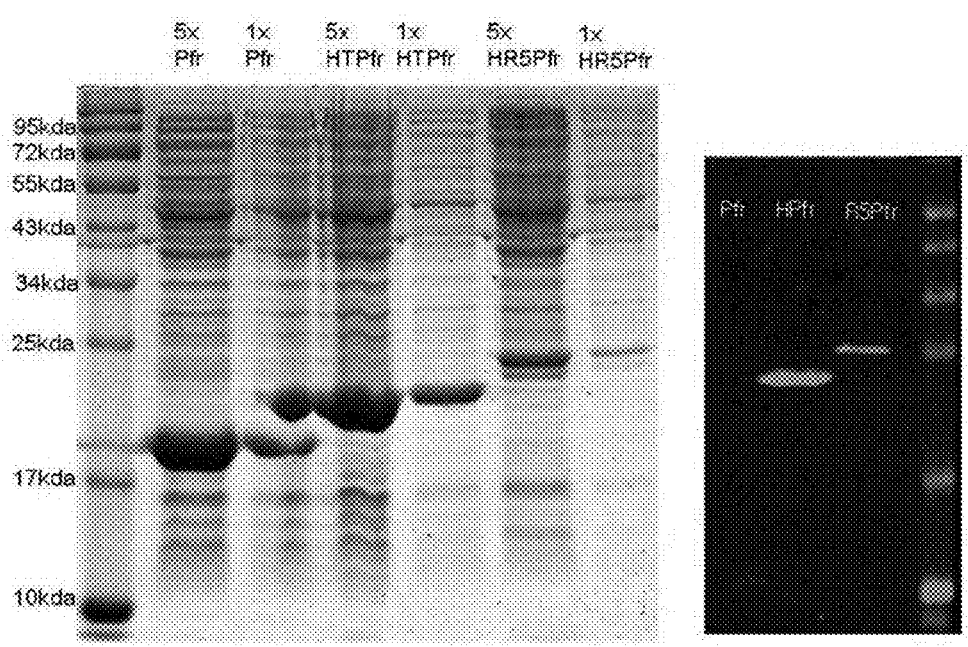
FIG. 12 shows the SDS-PAGE and Western blotting results of fusion proteins according to the present invention.

The expected molecular weights of the ferritin alone, the His-tagged ferritin and the R5-ferritin were 19 kDa, 21 kDa, and 23 kDa, respectively, and determined using the molecular weight ladders obtained by electrophoretic results. As a result, it was revealed that the molecular weights of the ferritin alone, the His-ferritin and the R5-ferritin were calculated to be 18.8 kDa, 21.7 kDa and 24.7 kDa, respectively, which were substantially identical to the expected molecular weights (FIG. 12). The ferritin protein was overexpressed in a soluble form regardless of the presence of the His-tag sequence.

The R5-ferritin was expressed in both of a soluble form and the form of an insoluble inclusion body. In this case, it was revealed that the R5-ferritin in the insoluble form was expressed at a higher expression level (not shown). Considering the amount of the soluble ferritin, the R5-ferritin was expressed at an expression level approximately 5 times lower than the other soluble ferritins, and both the His-tagged and His tag-free ferritins were expressed at a similar expression level (FIG. 12). The His tag-free ferritin was not detected through Western blotting since the tag-free ferritin did not react against an anti-His tag antibody, and only the His-tagged ferritin and the R5-ferritin were detected.

Example 5

Silica Synthesis Activities of Expressed Ferritins

Figure 13:
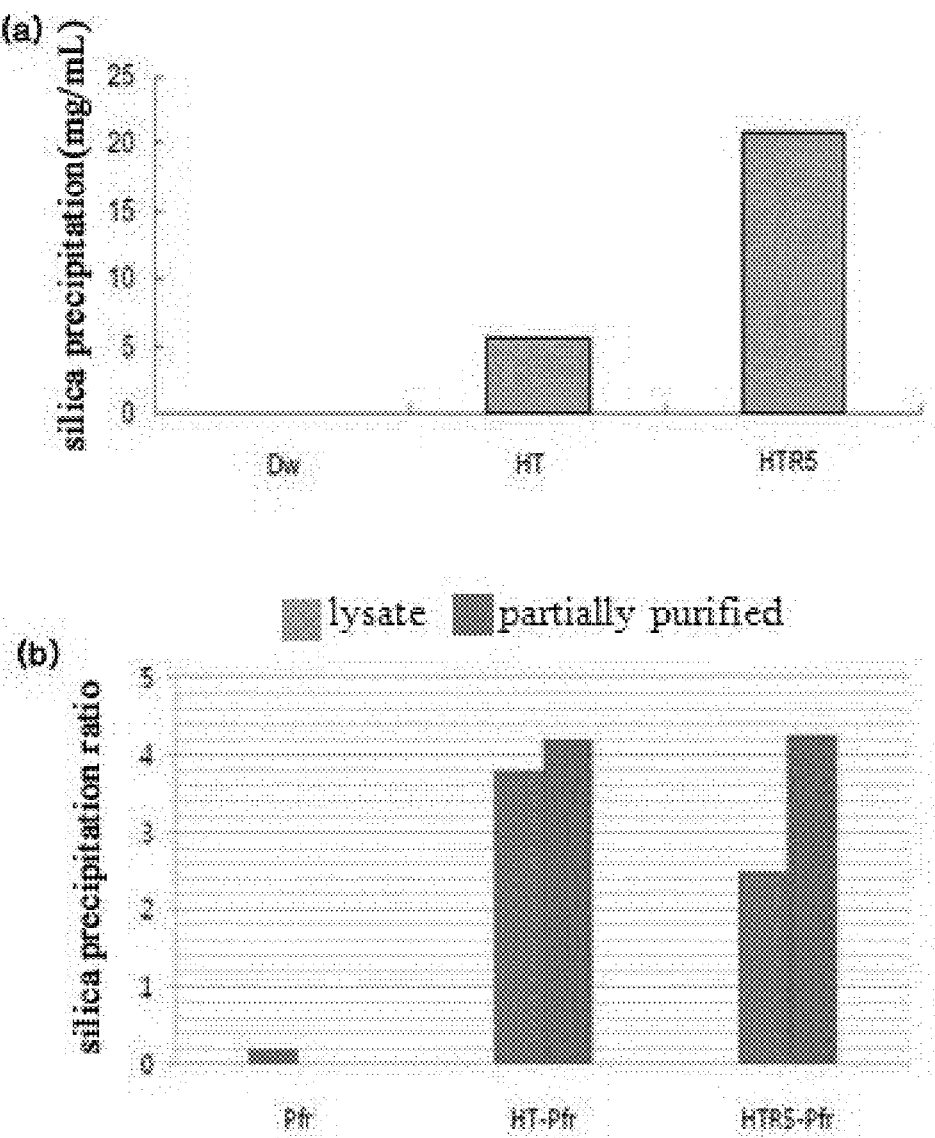
FIG. 13 shows silica synthesis activities of fusion proteins according to the present invention: a) shows silica precipitation activities caused by a peptide alone, and b) shows silica precipitation ratios normalized with an amount of an expressed protein.

A ferritin eluate partially purified using a cobalt affinity column was concentrated using an Amicon Ultra-0.5 mL filter. The cell homogenate was directly used without concentration to determine their activities. To compare the activities of the peptide itself that was bound to the ferritin structure, a peptide used as a His-tag sequence (MGSSHHHHHHSQDP; HT: SEQ ID NO: 9) and a His-tagged R5 peptide (MGSSH-HHHHHSQDP SSKKSGSYSGSKGSKRRIL; HTR5: SEQ ID NO: 10) were requested to be synthesized by Peptron Co. (Daejeon, Korea). The silica synthesis activities of the fusion proteins of ferritin and the respective peptides are shown in FIG. 13.

As shown in FIG. 13A, when the HT peptide was used alone, the HT peptide showed very low silica synthesis activities, but a precipitation rate of the ferritin increased when the HT peptide was fused with the ferritin. When the HTR5 was in the form of a peptide, the silica precipitated rapidly, and a precipitation rate of the HTR5 tended to slightly decrease when the HTR5 was fused with the ferritin. From these results, it seemed that there was a difference in precipitation rate and coating pattern of the silica according to the peptides to be fused.

Also, when the protein was partially purified and reacted, the silica synthesis activities of the HTR5-Pfr increased to a similar level to those of the HT-Pfr, as shown in FIG. 13B. The purities of the peptides were considered to be important for synthesis of the HTR5-Pfr. Since the probability of expressing the ferritin in a soluble form could be lowered according to the length of the peptide to be fused with the ferritin protein, it was noted that it was important to choose a peptide having a proper length so that the ferritin can be expressed in a soluble form and show excellent silica synthesis activities.

Example 6

Preparation of New Peptide-Ferritin Fusion Protein

In still another example of the fusion, the peptides for synthesizing silica was fused with a *H. pylori*-derived ferritin protein that was a ferritin protein forming a self-assembled sphere structure with a diameter of 12 nm. By way of representative example, EctP2 was used to be fused with the ferritin in the method similar to that of Example 4. A schematic view of an expression vector including the fusion protein is shown in FIG. 14A, and an optical microscope image of the silica aggregate formed by the fusion protein of ferritin and peptide for synthesizing silica through autoencapsulation is also shown in FIG. 14B.

Figure 14:
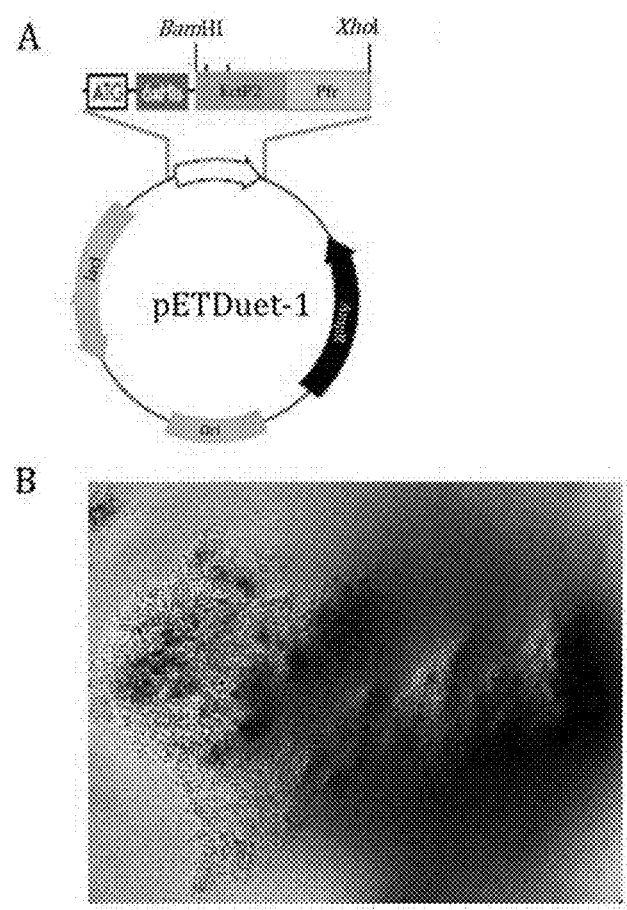
FIG. 14 shows (A) a EctP2-ferritin synthesis vector according to the present invention, and (B) an optical microscope image of silica synthesized by an EctP2-ferritin fusion protein.

As shown in FIG. 14, the fusion protein formed a spherical silica structure.

While the present invention has been shown and described with reference to certain exemplary embodiments thereof, it will be understood by those skilled in the art that various changes in form and details may be made therein without departing from the scope of the invention as defined by the appended claims.

Therefore, it will be understood that the practical scope of the present invention is defined by the appended claims and equivalents thereof.

The present invention has an effect of providing a peptide for synthesizing silica as a new silica biomaterial, which is derived from marine species.

Also, the present invention can be useful in synthesizing multifunctional silica in an aqueous weak-base solution under conditions of normal temperature and normal pressure using the peptide for synthesizing silica, thereby solving the prior-art problems regarding production of environmentally harmful by-products.

The peptide for synthesizing silica according to the present invention may form a self-assembled structure during silica synthesis, and thus may form a structure in which silica surrounds the surface of the self-assembled structure. Such a structure may serve as a delivery system used to deliver metal ions, isotopes or drugs, and can adjust solubility and porosity by mixing proper organic/inorganic components upon silica coating.

Also, the silica-based complex can be used for target-directed image diagnosis, treatment, biomolecule detection and drug delivery through binding to an enzyme, a functional ligand, a drug, etc.

According to the present invention, a novel silica biomaterial can serve as a delivery system used to deliver metal ions, isotopes or drugs, and can be used for target-directed image diagnosis, treatment, biomolecule detection and drug delivery through binding to an enzyme, a functional ligand, a drug, etc.

What is claimed is:

1. A method of synthesizing silica, comprising:
reacting a silica precursor with at least one peptide, wherein said peptide is selected from the group consisting of amino acid sequences set forth in SEQ ID NOs: 1 to 7, and a fusion protein thereof, wherein said fusion protein comprises a self-assembling protein and at least one peptide selected from the group consisting of amino acid sequences set forth in SEQ ID Nos: 1 to 7.

2. The method of claim 1, wherein the reacting is performed in an aqueous solution of pH 6 to 8 under conditions of normal temperature and a normal pressure.

3. The method of claim 1, wherein the reacting is performed in the aqueous solution further comprising an enzyme or a binding peptide, wherein the binding peptide is at least one selected from the group consisting of an antibody, a peptide specifically binding to DNA or RNA, or a receptor.

4. The method of claim 1, wherein the reacting is performed in the aqueous solution further comprising a nanotube or a nanomesh.

5. The method of claim 1, wherein the reacting is performed in the aqueous solution further comprising a phospholipid.

6. The method of claim 1 or 5, wherein the reacting is performed for preparing a single silica film by allowing at least one peptide selected from the group consisting of amino acid sequences set forth in SEQ ID NOs: 1 to 7, a silica precursor and a phospholipid to react with each other, or synthesizing a porous silica by allowing the peptide, the silica precursor and the phospholipid to react with each other to prepare an organic/inorganic complex, and treating the organic/inorganic complex with heat or an organic solvent to remove an organic substance.

7. The method of claim 1, wherein the reacting is performed in the aqueous solution further comprising hydroxyapatite.

* * * * *